United States Patent
Petersen et al.

(10) Patent No.: US 6,759,044 B1
(45) Date of Patent: Jul. 6, 2004

(54) CRYPTOPAIN ANTIBODIES FOR PROPHYLAXIS, TREATMENT, DIAGNOSIS AND DETECTION OF CRYPTOSPORIDIUM SPECIES

(75) Inventors: Carolyn Petersen, Berkeley, CA (US); Jin-Xing Huang, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/598,062

(22) Filed: Jun. 20, 2000

Related U.S. Application Data

(62) Division of application No. 08/827,171, filed on Mar. 27, 1997.
(60) Provisional application No. 60/014,233, filed on Mar. 27, 1996.

(51) Int. Cl.[7] .................. A61K 39/395; A61K 39/40
(52) U.S. Cl. .................. 424/139.1; 424/141.1; 424/164.1

(58) Field of Search .................. 424/139.1, 141.1, 424/164.1, 187.1

(56) References Cited

U.S. PATENT DOCUMENTS 5,817,310 A * 10/1998 Ramakrishnan et al.

OTHER PUBLICATIONS

Nesterenko et al. *Microbios*, vol. 83, pp. 77–88, 1995.*

* cited by examiner

*Primary Examiner*—Gary Kunz
*Assistant Examiner*—Stephen Gucker
(74) *Attorney, Agent, or Firm*—Hana Verny; Peters, Verny, Jones & Schmitt, LLP

(57) ABSTRACT

Vaccines, antibodies, proteins, DNAs and RNAs for diagnosis, prophylaxis, treatment and detection of Cryptosporidium species or Cryptosporidium species infections. Cryptosporidium species antigen and DNAs and RNA encoding the Cryptosporidium antigen and fragments thereof and recombinant proteins or fusion proteins produced thereby. Methods for diagnosis, prophylaxis, treatment and detection of Cryptosporidium species infections.

2 Claims, 10 Drawing Sheets

FIG. 2-A

```
1/1                                          31/11
CAA AAC TTC CTA ATT TCT CAA TGT ATT ACT AAT TAA TAG AAA GTT TGT TTT ATT TTC ATG
gln asn phe leu ile ser gln cys ile thr asn OCH AMB lys val cys phe ile phe met
61/21                                        91/31
TGG ATA AAT GAA TTA TTT TCT CTA TAC CGG CAT TTG CAT GCA ATT TTG TAT GAC TAA AAT
trp ile asn glu leu phe ser leu tyr arg his leu his ala ile leu tyr asp OCH asn
121/41                                       151/51
GTA AAT AAT TAT TTG CAT GCA ATT ATG TGG GCA TGT CAT AGT TTT TCA AGA ATA ATA ATA
val asn asn tyr leu his ala ile met trp ala cys his ser phe ser arg ile ile ile
181/61                                       211/71
AGA TGA CAT GAC AAG ATA TTC AAA AAA ATT TGA TGA TTA TAT GTT GAA GTT AAT TGA ACT
arg OPA his asp lys ile phe lys lys ile OPA OPA leu tyr val glu val asn OPA thr
241/81                                       271/91
AAA AAG TAA TTA AGT AAA ATG GAC ATA GGA AAC AAC GTG GAA GAA CAT CAG GAA TAT ATT
lys lys OCH leu ser lys met asp ile gly asn asn val glu glu his gln glu tyr ile
301/101                                      331/111
TCT GGA CCA TAC ATT GCA TTA ATT AAT GGC ACT AAT CAA CAA AGG GAA CCG AAT AAA AAG
ser gly pro tyr ile ala leu ile asn gly thr asn gln gln arg glu pro asn lys lys
361/121                                      391/131
TTG AAA AAC ATA ATA ATT GCA ACG TTG ATT GCA ATC TTT ATA GTT TTG GTT GTT ACT GTA
leu lys asn ile ile ile ala thr leu ile ala ile phe ile val leu val val thr val
421/141                                      451/151
TCT TTG TAT ATT ACT AAT AAC ACC AGT GAC AAA ATT GAC GAT TTC GTA CCT GGT GAT TAT
ser leu tyr ile thr asn asn thr ser asp lys ile asp asp phe val pro gly asp tyr
481/161                                      511/171
GTT GAT CCA GCA ACT AGG GAG TAT AGA AAG AGT TTT GAG GAG TTC AAA AAG AAA TAC CAC
val asp pro ala thr arg glu tyr arg lys ser phe glu glu phe lys lys lys tyr his
541/181                                      571/191
AAA GTA TAT AGC TCT ATG GAG GAG GAA AAT CAA AGA TTT GAA ATT TAT AAG CAA AAT ATG
lys val tyr ser ser met glu glu glu asn gln arg phe glu ile tyr lys gln asn met
601/201                                      631/211
AAC TTT ATT AAA ACA ACA AAT AGC CAA GGA TTC AGT TAT GTG TTA GAA ATG AAT GAA TTT
asn phe ile lys thr thr asn ser gln gly phe ser tyr val leu glu met asn glu phe
661/221                                      691/231
GGT GAT TTG TCG AAA GAA GAG TTT ATG GCA AGA TTC ACA GGA TAT ATA AAA GAT TCC AAA
gly asp leu ser lys glu glu phe met ala arg phe thr gly tyr ile lys asp ser lys
721/241                                      751/251
GAT GAT GAA AGG GTA TTT AAG TCA AGT AGA GTC TCA GCA AGC GAA TCA GAA GAG GAA TTT
asp asp glu arg val phe lys ser ser arg val ser ala ser glu ser glu glu glu phe
781/261                                      811/271
GTT CCC CCA AAT TCT ATT AAT TGG GTG GAA GCT GGA TGC GTG AAC CCA ATA AGA AAT CAA
val pro pro asn ser ile asn trp val glu ala gly cys val asn pro ile arg asn gln
841/281                                      871/291
AAG AAT TGT GGG TCA TGT TGG GCT TTC TCT GCT GTT GCA GCT TTG GAG GGA GCA ACG TGT
lys asn cys gly ser cys trp ala phe ser ala val ala ala leu glu gly ala thr cys
901/301                                      931/311
GCT CAA ACA AAC CGA GGA TTA CCA AGC TTG AGT GAA CAG CAA TTT GTT GAT TGC AGT AAA
ala gln thr asn arg gly leu pro ser leu ser glu gln gln phe val asp cys ser lys
```

FIG. 2-B

```
961/321                                         991/331
CAA AAT GGC AAC TTT GGA TGT GAT GGA GGA ACA ATG GGA TTG GCT TTT CAG TAT GCA ATT
gln asn gly asn phe gly cys asp gly gly thr met gly leu ala phe gln tyr ala ile
1021/341                                        1051/351
AAG AAC AAA TAT TTA TGT ACT AAT GAT GAT TAC CCT TAC TTT GCT GAG GAA AAA ACA TGT
lys asn lys tyr leu cys thr asn asp asp tyr pro tyr phe ala glu glu lys thr cys
1081/361                                        1111/371
ATG GAT TCA TTT TGC GAG AAT TAT ATA GAG ATT CCT GTA AAA GCC TAC AAA TAT GTA TTT
met asp ser phe cys glu asn tyr ile glu ile pro val lys ala tyr lys tyr val phe
1141/381                                        1171/391
CCG AGA AAT ATT AAT GCA TTA AAG ACT GCT TTG GCT AAG TAT GGA CCA ATT TCA GTT GCA
pro arg asn ile asn ala leu lys thr ala leu ala lys tyr gly pro ile ser val ala
1201/401                                        1231/411
ATT CAG GCC GAT CAA ACC CCT TTC CAG TTT TAT AAA AGT GGA GTA TTC GAT GCT CCT TGT
ile gln ala asp gln thr pro phe gln phe tyr lys ser gly val phe asp ala pro cys
1261/421                                        1291/431
GGA ACC AAG GTT AAT CAT GGA GTT GTT CTA GTT GAA TAT GAT ATG GAT GAA GAT ACT AAT
gly thr lys val asn his gly val val leu val glu tyr asp met asp glu asp thr asn
1321/441                                        1351/451
AAA GAA TAT TGG CTA GTA AGA AAT AGC TGG GGT GAA GCG TGG GGA GAG AAA GGA TAC ATC
lys glu tyr trp leu val arg asn ser trp gly glu ala trp gly glu lys gly tyr ile
1381/461                                        1411/471
AAA CTA GCT CTT CAT TCT GGA AAG AAG GGA ACA TGT GGT ATA TTG GTT GAG CCA GTG TAT
lys leu ala leu his ser gly lys lys gly thr cys gly ile leu val glu pro val tyr
1441/481                                        1471/491
CCA GTG AAT AAT CAA TCA ATA TAA GCA TTT CAG TGT TTG ACT AAG TAA TTC TAA TAT ATT
pro val ile asn gln ser ile OCH ala phe gln cys leu thr lys OCH phe OCH tyr ile
1501/501                                        1531/511
TCA GCA TTC TCA GAG ATA ATT TTA GTT CAA ATG AAC AAT CTA TTC ATA TAT ATA AGC ATT
ser ala phe ser glu ile ile leu val gln met asn asn leu phe ile tyr ile ser ile
1561/521                                        1591/531
CCA TAC TTA ATT ATT TAT TGA TTT TAA TAA AAT GTT TGG CTA AAG AAA GCA ATC AAG ATA
pro tyr leu ile ile tyr OPA phe OCH OCH asn val trp leu lys lys ala ile lys ile
1621/541                                        1651/551
ATT TAT GGA CGT TCT ATT GTT CTT ACT TCA ATA ATA ATC CTT
ile tyr gly arg ser ile val leu thr ser ile ile ile leu
```

FIG. 3-A

```
met asp ile gly asn asn val glu glu his gln glu tyr ile ser
 1               5                    10                  15
gly pro tyr ile ala leu ile asn gly thr asn gln gln arg glu
                20                   25                  30
pro asn lys lys leu lys asn ile ile ile ala thr leu ile ala
                35                   40                  45
ile phe ile val leu val val thr val ser leu tyr ile thr asn
                50                   55                  60
asn thr ser asp lys ile asp asp phe val pro gly asp tyr val
                65                   70                  75
asp pro ala thr arg glu tyr arg lys ser phe glu glu phe lys
                80                   85                  90
lys lys tyr his lys val tyr ser ser met glu glu glu asn gln
                95                  100                 105
arg phe glu ile tyr lys gln asn met asn phe ile lys thr thr
               110                  115                 120
asn ser gln gly phe ser tyr val leu glu met asn glu phe gly
               125                  130                 135
asp leu ser lys glu glu phe met ala arg phe thr gly tyr ile
               140                  145                 150
lys asp ser lys asp asp glu arg val phe lys ser ser arg val
               155                  160                 165
ser ala ser glu ser glu glu glu phe val pro pro asn ser ile
               170                  175                 180
asn trp val glu ala gly cys val asn pro ile arg asn gln lys
               185                  190                 195
asn cys gly ser cys trp ala phe ser ala val ala ala leu glu
               200                  205                 210
gly ala thr cys ala gln thr asn arg gly leu pro ser leu ser
               215                  220                 225
glu gln gln phe val asp cys ser lys gln asn gly asn phe gly
               230                  235                 240
cys asp gly gly thr met gly leu ala phe gln tyr ala ile lys
               245                  250                 255
asn lys tyr leu cys thr asn asp asp tyr pro tyr phe ala glu
               260                  265                 270
glu lys thr cys met asp ser phe cys glu asn tyr ile glu ile
               275                  280                 285
pro val lys ala tyr lys tyr val phe pro arg asn ile asn ala
               290                  295                 300
leu lys thr ala leu ala lys tyr gly pro ile ser val ala ile
               305                  310                 315
gln ala asp gln thr pro phe gln phe tyr lys ser gly val phe
               320                  325                 330
asp ala pro cys gly thr lys val asn his gly val val leu val
```

FIG. 3-B

```
                  335                      340                          345
   glu tyr asp met asp glu asp thr asn lys glu tyr trp leu val
                      350                      355                      360
   arg asn ser trp gly glu ala trp gly glu lys gly tyr ile lys
                      365                      370                      375
   leu ala leu his ser gly lys lys gly thr cys gly ile leu val
                      380                      385                      390
   glu pro val tyr pro val ile asn gln ser ile
                      395                      400 403    SEQ ID NO: 4
```

FIG. 4

```
Papain      ..........  ..........  ..........  .......MAM  IPSISKLLFV  AICLFVYMGL   60
Cryptopain  MDIGNNVEEH  QEYISGPYIA  LINGTNQQRE  PNKKLKNIII  ATLIAIFIVL  VVTVSLYITN
P.v., mature ..........  ..........  ..........  ..........  ..........  ..........  130

SFGDFSI.VG  YSQNDLTSTE  RLIQLFESWM  LKHNKIYKNI  DEKIYRFEIF  KDNLKYIDET  NKKNNSYWLG
NTSDKIDDFV  PGDYVDPATR  EYRKSFEEFK  KKYHKVYSSM  EEENQRFEIY  KQNMNFIKTT  NSQGFSYVLE
..........  ..........  ..........  ..........  ..........  ..........  ..........  200

LNVFADMSND  EFKEKYTGSI  AGNY....TT  TELSYEEVLN  DGDVNIPEYV  DWRQKGAVTP  VKNQGSCGSC
MNEFGDLSKE  EFMARFTGYI  KDSKDDERVF  KSSRVSASES  EEEFVPPNSI  NWVEAGCVNP  IRNQKNCGSC
..........  ..........  ..........  ..........  ....FPDSR  DYRSKFNFLP  PKDQGNCGSC
                                                                        CGSC        270

WAFSAVVTIE  GIIKIRTG.N  LNEYSEQELL  DCDR..RSYG  CNGGYPWSAL  QLVAQY.GIH  YRNTYPYEGV
WAFSAVAALE  GATCAQTNRG  LPSLSEQQFV  DCSKQNGNFG  CDGGIMGLAF  QYAIKNKYLC  TNDDYPYFAE
WAFAAIGNFE  YLYVHTRHEM  PISFSEQQMV  DCST..ENYG  CDGGNPFYAF  LYMINN.GVC  LGDEYPYKGH
WAF                                                                                 340

QRYC.RSREK  GPYAAKTDGV  RQVQPYNEGA  LLYSIAN..Q  PVSVVLEAAG  KDFQLYRGGI  FVGPCGNKVD
EKTCMDSFCE  NYIEIPVKAY  KYVFPRNINA  LKTALAKY.G  PISVAIQADQ  TPFQFYKSGV  FDAPCGTKVN
EDFFCLNYRC  SLLGRVHFIG  DVKPNELIMA  L.....NYVG  PVTIAVGA.S  EDFVLYSGGV  FDGECNPELN
                                                                                    410

HAVAAVGYGP  ..........  ..........  ..........  .NYILI  KNSWGTGWG  ENGYIRIKRG
HGVVLVGYDM  DEDTNKE...  ..........  ..........  YWLV  RNSWGEAWG  EKGYIKLALH
HSVLLVGYGQ  VKKSLAFEDS  HSNVDSNLIK  KYKENIKGDD  DDDIIYYWIV  RNSWGPNWG  EGGYIRIKRN
                                                              YWLV  RNSW

TGNSYGVCGL  YTSSFYPVKN  ...                      SEQ ID NO: 7
.SGKKGTCGI  LVEPVYPVIN  QSI
KAGDDGFCGV  GSDVFFPIY.  ...                      SEQ ID NO: 8
433
```

FIG. 6
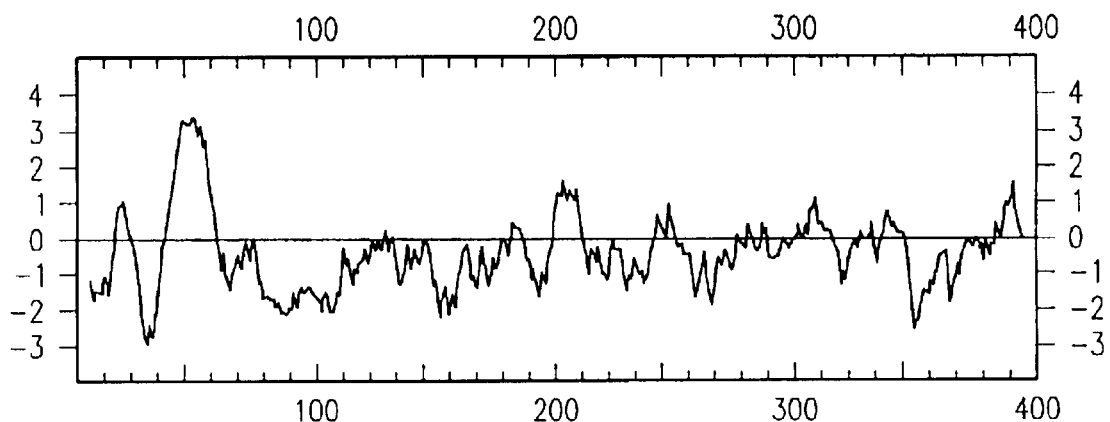
FIG. 7A
1. AAAGGATCCT GC/TGGIA/TG/CITG C/TTGGGCITT
2. TTTGAATTCC CAIG/CA/TA/GTTIC/T T/GIAC/TIATCCA A/GTA
1. CCAGGTACCA TGGACATAGG AAAC
2. CCCTCTAGAT GCTTATATTG ATTG
FIG. 7B
FIG. 8
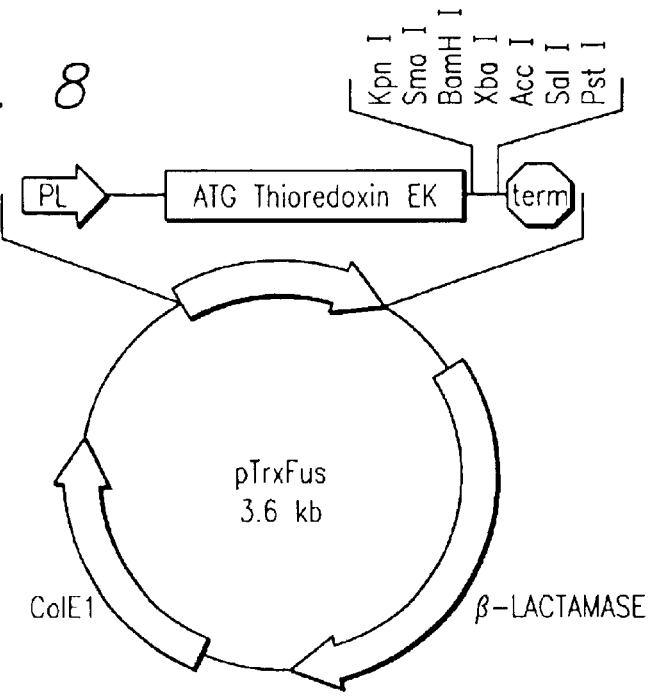

CRYPTOPAIN ANTIBODIES FOR PROPHYLAXIS, TREATMENT, DIAGNOSIS AND DETECTION OF CRYPTOSPORIDIUM SPECIES

This application is a Divisional application of Ser. No. 08/827,171, filed Mar. 27, 1997, allowed, which is This application is a based on the provisional application Ser. No. 60/014233 filed on Mar. 27, 1996.

This invention was developed partially with U.S. Government support under National Institutes of Health Grant No U01-AI35123. The U.S. Government may have certain rights in this invention.

BACKGROUND OF THE INVENTION

1. Field of the Invention

This invention concerns vaccines, antibodies, proteins, DNAs and RNAs for diagnosis, prophylaxis and treatment of Cryptosporidium species infections and for detection of Cryptosporidium species. In particular, this invention concerns Cryptosporidium species antigen comprised of a protein, as well as polyclonal and monoclonal antibodies directed against the antigen, DNAs and RNA encoding the Cryptosporidium species antigen and fragments and analogs thereof, and methods for production of recombinant or fusion proteins. This invention also concerns methods for diagnosis, prophylaxis, treatment of Cryptosporidium infections and detection of Cryptosporidium species.

2. Background and Related Disclosures

The genus Cryptosporidium consists of Apicomplexan parasites that invade and develop within epithelial cells of the gastrointestinal, hepatobiliary and respiratory tracts of a wide variety of vertebrates including reptiles, birds and mammals. Cryptosporidium was recognized as a cause of animal disease for several decades before the first cases of human cryptosporidiosis were reported in 1976. However, it was not until 1982 that the magnitude of disease caused by this parasite in both AIDS patients and immunocompetent hosts began to be appreciated. Subsequently, Cryptosporidium has been found to be one of the most common causes of human diarrhea worldwide, and to be an increasingly recognized cause of diarrhea in children, animal care workers, and travelers. (*Cryptosporidium and Cryptosporidiosis in Humans*, Ed. Fayer, R., CRC Press, Boca Raton (1997)).

Large waterborne outbreaks of cryptosporidiosis caused by contaminated municipal water supplies in the US or in the UK have been noted in the last ten years (*N. Enal. J. Med.*, 320:1372 (1989), and 33:161 (1994)). The most recent outbreak in Milwaukee in April 1993 involved 400,000 persons and led to the subsequent deaths of more than 100 immunocompromised persons. Like a number of other waterborne outbreaks, the Milwaukee outbreak appears to have been due to contamination from farm or abattoir run-off and specifically to cryptosporidiosis among cows/calves. Nosocomial transmission in hospitals from patients to staff, patient to patient, and contaminated ice to patients and staff have also been well documented (*J. Infect. Dis.*, 158:647 (1985)).

Waterborne and nosocomial spread uncovered a number of biological characteristics of oocysts. First, the infectious dose of a parasite is very low. The $ID_{50}$ for human volunteers with normal immune systems is 132 oocysts *N. Engl. J. Med.*, 332:855 (1995). Second, infected hosts, for example calves, excrete large numbers of oocysts, on the order of $10^{10}$/day. Third, the oocysts are fully sporulated and ready to infect when excreted. Fourth, the oocysts are environmentally hardy. They remain infectious in cool, moist areas for 3–4 months. They are not killed by chlorine levels achievable in drinking water. Fifth, the oocysts are quite small, 4–6 μm, and are thus difficult to filter.

The clinical importance of cryptosporidiosis has increased markedly with the recognition of a life-threatening form of the disease in patients with immunodeficiency disorders such as AIDS, hypogammaglobulinaemia, and chemotherapeutic immunosuppression. The prevalence of cryptosporidiosis in AIDS patients in the US is estimated to be 5–10% and in central Africa 40%. Immunodeficient patients may have fulminant cryptosporidial diarrhea that may persist until death, whereas the diarrhea of immunocompetent patients is self-limited and rarely lasts more than 2–4 weeks. Cholera-like diarrhea is common in immunocompromised patients with reported losses of up to 17 liters per day. Hepatobiliary disease may result in severe abdominal pain and nausea. Removal of immunosuppression in chemotherapy patients leads to resolution of the diarrhea. Some AIDS patients with cryptosporidiosis will be able to eliminate the parasite by induction of anti-retroviral therapy (*Am. Intern. Med.*, 116:840 (1992)).

Among those who develop disease, a quarter have CD4 counts greater than 209, suggesting that the disease may occur relatively early in the course of HIV disease (*Am. J. Epidemiol.*, 144:807 (1996). Unfortunately, few details about the biology and molecular mediators of the disease process have been described and so far no effective therapy has been discovered.

The infective forms of Cryptosporidium, called sporozoites and merozoites, appear to adhere to the host cell and release the contents of anterior organelles (rhoptries, micronemes or dense granules) during the invasion process (*Parasitol. Today*, 8:28(1992)). Proteins involved in these events have in many instances been found to be the target of invasion blocking immunity in vitro and neutralization in vivo (*Infect. Immun.*, 56:2538(1988)).

Active and passive immunization studies using malaria and Toxoplasma challenged or infected hosts have shown that certain secreted components of the apical complex organelles are the target of protective antibodies. In some cases, as for example in the case of the circumsporozoite and merozoite surface proteins of malaria, these antigens are under development as vaccines.

While the actual interaction between cryptosporidium and the host's immune system is poorly understood, it is known that disruption of either the cellular or the humoral components can result in protracted cryptosporidiosis (*Parasitol. Today*, 8:24 (1992)). However, specific antibodies alone appear to be enough to neutralize the organism's infectivity. In vitro and in vivo observations indicate that antibodies to *Cryptosporidium parvum* inhibit invasion and intracellular development leading to protection in challenge experiments, or amelioration of infection in established disease (*Infect. Immun.*, 59:1172 (1991)).

One source of such antibodies is hyperimmune bovine colostrum (HBC) collected from cows immunized with Cryptosporidium oocysts. Calves challenged with Cryptosporidium oocysts are protected from the development of disease by the administration of HBC (*Infect. Immun.*, 61:4079 (1993)). Some immunocompromised AIDS patients infected with Cryptosporidium have also responded to HBC with a reduction in or disappearance of the symptoms of the disease (*Gastroenterology*, 98:486 (1990)). Immunoglobulin from HBC (HBC Ig) has been found to inhibit the ability of the sporozoite to invade and/or develop intracellularly in vitro and it has been used to immunoprecipitate at least 22 different surface radioiodinated proteins of Cryptosporidium sporozoites. Western blot analysis of proteins of whole oocysts which contain sporozoite, indicates that HBC predominantly recognizes two proteins of sizes 250 Kd and >900 Kd (*Infect. Immun.*, 61:4079 (1993)).

The use of HBC for human use is problematic. HBC produced using whole oocysts is batch dependent and this may lead to the development of passive immune preparations which are not uniform in immunogenicity and potency. This generates a problem when these immune preparation are to be administered to human patients as such non-uniformity may result in failure of protection. In addition, it would be desirable to allow preparation of large amounts of antigen expressed in heterologous systems than to purify oocyst.

Thus, there is a continuous need for immunogenic agents which are reasonably reproducible and have uniform and controllable immunogenicity and potency which agents would be useful for the immunotherapy of cryptosporidiosis in both uncompromised and immunocompromised subjects, such as AIDS patients, and would allow the prophylaxis and treatment of cryptosporidiosis.

Additionally, there is a need to have available methods for reproducible expression of specific target for Cryptosporidium antigen in large amounts, which antigen would provide a better immunogen. This approach requires that a specific Cryptosporidium antigen is cloned and identified as a potential candidate through its ability to elicit an antibody response that is immunoprotective. Before antibodies produced in this manner are tested in or administered to humans or animals, testing in in vitro assay of their inhibitory effect on invasion or intracellular development of the Cryptosporidium organism in cultured cells and in vivo studies would be desirable.

It is, therefore, a primary objective of this invention to provide Cryptosporidium cryptopain polyclonal or monoclonal antibodies and vaccines to be used for prophylaxis, treatment, diagnosis and detections of cryptosporidiosis and to express a portion of the cryptopain sequence/locus to provide target protein antigens allowing production of recombinant anti-Cryptosporidium vaccines and passive immune products.

All patents, patent applications and publication cited herein are hereby incorporated by reference.

SUMMARY OF THE INVENTION

One aspect of this invention concerns vaccines, antigens, antibodies, proteins, DNAs and RNAs for prophylaxis, treatment and detection or diagnosis of Cryptosporidium species or Cryptosporidium species infections.

Another aspect of this invention concerns a Cryptosporidium antigen protein comprising pre, pro, and mature enzyme sequences and their fragments.

Still another aspect of this invention concerns polyclonal or monoclonal antibodies directed against the cryptosporidium antigen.

Still yet another aspect of this invention concerns a DNA and RNA encoding the Cryptosporidium antigen and fragments thereof and the antigen pre, pro, and mature regions.

Another aspect of this invention concerns a polyclonal or monoclonal antibodies directed against invasive stages of Cryptosporidial species capable of preventing and ameliorating invasion of Cryptosporidium infection.

Still another aspect of this invention concerns a natural, synthetic or recombinant vaccine useful for active immunization of animals and humans against Cryptosporidium infection.

Still another aspect of this invention concerns a natural, synthetic or recombinant protein useful for preparation of passive immune products for treatment of established infection.

Another aspect of this invention concerns a natural, synthetic or recombinant DNA vaccine capable of endogenous production of inhibitory amount of anti-*Cryptosporidium parvum* antibodies.

Another aspect of this invention concerns a natural, synthetic or recombinant RNA vaccine capable of endogenous development of inhibitory amount of anti-*Cryptosporidium parvum* antibodies.

Still another aspect of the invention concerns a method for use of a pre pro enzyme portion of the cysteine proteinase molecule as a competitive inhibitor of the action of the mature enzyme.

Still yet another aspect of the invention is the use of antigen, antibody, DNA or RNA to detect the presence of the cysteine proteinase or antibodies to cysteine proteinase, or DNA or RNA encoding the cysteine proteinase, for diagnosis in a human or animal host or detection in the environment.

Another aspect of this invention concerns the sequence of a 401 amino acid protein comprising a cathepsin L-like cysteine proteinase of MW 45 kDa present in sporozoites and merozoites, and its amino acid and size variants including a deduced mature 226 amino acid protein of MW 25 kDa.

Another aspect of this invention concerns the DNA sequence of 1203 nucleotides encoding the 45 kDa protein, the cathepsin-like cysteine proteinase, cryptopain, its nucleotide and size variants and its upstream regulatory elements.

Another aspect of this invention concerns the RNA sequence determined by the DNA sequence of cryptopain and its nucleotide and size variants including polyadenylation sequence.

still yet another aspect of this invention concerns a group of cryptopain recombinant or expressed protein targets of polyclonal antibodies which inhibit Cryptosporidium infection, invasion, or adhesion.

Another aspect of this invention concerns a method for prophylaxis and treatment of Cryptosporidium or Cryptosporidium infections using vaccines, antibodies, proteins, DNAs and RNAs of the invention.

Still yet another aspect of this invention concerns a method of prophylaxis, treatment, inhibition or retardation of a Cryptosporidium infection comprising administering to a subject in need of such treatment an amount of an anti-Cryptosporidium polyclonal or monoclonal antibodies prophylactically or therapeutically effective to provide immunity against infection or treatment for disease.

Still yet another aspect of this invention concerns a method of prophylaxis, treatment, retardation, or inhibition of Cryptosporidium infection comprising administering to a subject in need of such treatment a vaccine comprising the polypeptide of this invention or its DNA or RNA capable of endogenous stimulation of the production of inhibitory amount of anti-Cryptosporidium antibodies or protective cellular immune responses.

Still yet another aspect of this invention concerns a method for diagnosing Cryptosporidium infection of a subject, comprising steps:

(a) contacting a body specimen, fluid or tissue obtained from the subject with an anti-Cryptosporidium monoclonal or polyclonal antibody; and (b) detecting the formation of antibody-antigen complex wherein the presence of the complex indicates the presence of a Cryptosporidium organism in the subject.

Still yet another aspect of this invention concerns a method for detecting anti-Cryptosporidium antibody in a subject, said method comprising steps:

(a) contacting a body specimen, fluid or tissue obtained from the subject with the cryptopain; and (b) detecting a formation of antibody-antigen complex wherein the presence of the complex indicates the presence of a Cryptosporidium antibody in the subject.

Still another aspect of this invention is a Cryptosporidium diagnostic or detection kit comprising anti-Cryptosporidium specific monoclonal and polyclonal antibodies or antigen according to the invention and a means for detection of an antibody-antigen complex.

BRIEF DESCRIPTION OF THE DRAWINGS

FIG. 2 is the DNA sequence of cryptopain (SEQ ID NO: 1) comprising sequences encoding segments for the pre and pro regions (SEQ ID NO: 2), mature enzyme coding region (SEQ ID NO:. 3) and 3' and 5' flanking sequences.

FIG. 3 is the protein sequence of cryptopain (SEQ ID NO: 4) comprising segments for the pre and pro regions (SEQ ID NO: 5) and for mature enzyme (SEQ ID NO: 6).

FIG. 4 is an amino acid alignment showing marked amino acid similarities of cryptopain to other cathepsin-like cysteine proteinases (SEQ ID NOs: 4, 7 and 8).

FIG. 6 shows a Kyte Doolittle hydropathy plot indicating an N-terminal hydrophobic sequence consistent with membrane targeting and secretion of cryptopain.

FIG. 7 are oligonucleotide sequences used to generate DNA fragments of the cryptopain gene. FIG. 7A1 is a degenerate primer based on the conserved cysteine (sense) and FIG. 7A2 is a degenerate primer based on conserved arginine (antisense) of the *P. vinckei* cysteine proteinase gene. These primers were used to amplify the 459 bp fragment of cryptopain from *C. parvum* DNA. FIG. 7B shows primers used to directionally clone the entire *C. parvum* gene comprising pre, pro and mature protein encoding regions, to be expressed as a thioredoxin fusion protein. FIG. 7B1 is the sense and FIG. 7B2 is the antisense oligonucleotide.

FIG. 8 is a diagram of pTrxFus showing the directional cloning strategy.

FIG. 10 are graphs showing percentage of invasion/intracellular development of *Cryptosporidium parvum* sporozoites in vitro in MDCK cells in the presence of inhibitors of cysteine proteinases.

DEFINITIONS

Figure 1:
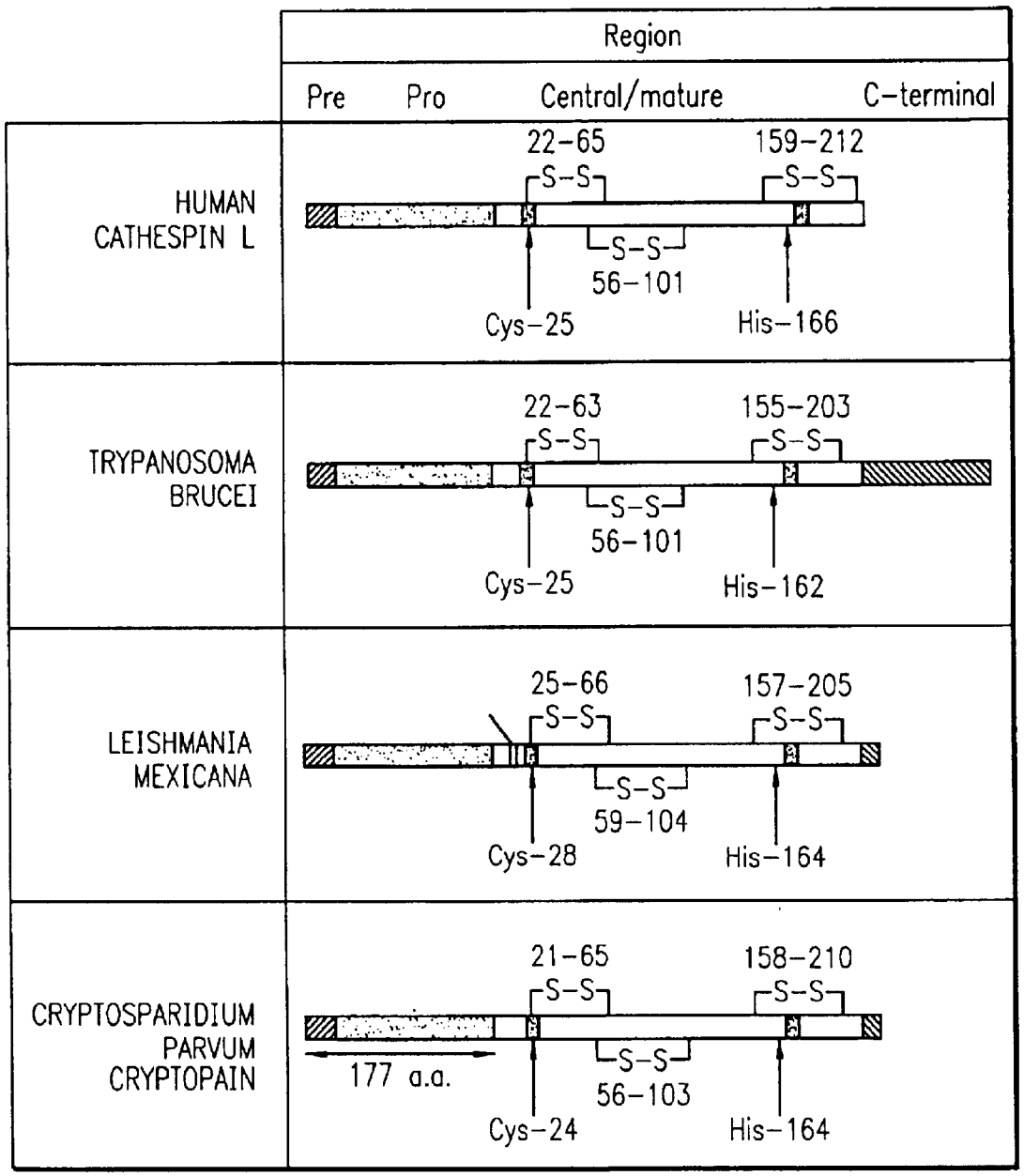
FIG. 1 is a diagram showing the strategy model for developing a probe for the Cryptosporidium cysteine proteinase using consensus oligonucleotide primers for PCR amplification of genomic DNA. The model is compared to previously published diagrams of the primary structure of cysteine proteinases from other organisms.

As used herein:

"Cryptopain" or "Cryptosporidium antigen" means a protein which is a cathepsin L-like cysteine proteinase having a function in invasion and infection of host cells by Cryptosporidium. Cryptopain is represented by a protein containing 401 amino acids and is identified as SEQ ID NO: 4 (FIG. 3) comprising a protein of MR 45 kDa. Homology to other cathepsin L-like cysteine proteinases seen in FIG. 4 indicates that the mature active enzyme is cleaved after amino acid 175 one residue N-terminal to a conserved prolines and comprises a 25 kDa protein of 226 amino acids. Cryptopain also includes size and sequence variance proteins which maintain the same function.

The "structure" or "structural characteristics" of cryptopain defines a protein, and DNA and RNA encoding the cryptopain protein and includes all structural variations, mutations and fragments exhibiting the same function.

The "functionality" or "functional characteristics" of cryptopain is defined by the action of the protein and structural variants described, such that infection and disease occurs.

"Inactive enzyme" means enzyme comprised either of mature enzyme regions and pro regions, or mature enzyme and pro and pre regions wherein the pro or pre pro regions are responsible for the mature enzyme nonfunctionality or for the inhibition of its function.

"Active enzyme" or "mature enzyme" means functional enzyme and is comprised of the mature region. Mature enzyme contains the catalytic active sites of the cysteine proteinase and typically begins with one residue N-terminal to a conserved proline.

"Pro" or "pro region" means the contiguous amino acid sequence which renders the mature enzyme inactive by its structural association with it.

"Pre" or "pre region" means the terminal amino acid sequence which is contiguous with the pro region and may contain a signal for trafficking movement of inactive enzyme in the cell.

"The gene" or "genes encoding cryptopain" means DNA encoding the cryptopain protein.

"Sporozoites or merozoites" mean any life stage which may invade or develop in the host cells and any variant or mutant of said life stages.

"Antibodies" means proteins which structurally interact with the target antigen and are produced when the antigen is introduced into an animal, such that they stimulate the immune system. The term also includes antibodies produced in vitro, such as chimeras, or hybridoma cell cultures, as well as hybridomas or chimeric constructs introduced into a host to provide an in vivo antibody.

"Antibodies to cryptopain" means proteins which structurally interact with the target antigen cryptopain and inhibit invasion, infection or development of the sporozoites or merozoites in the host cell.

"Monoclonal antibodies" means the monovalent antibodies produced by an B cell fused to an immortalized cell producing specific antibody to cryptopain.

"Polyclonal antibodies" means antibodies directed at cryptopain which are not monovalent and are the products of multiple B cells in character.

"Cryptosporidium antigen" means a protein with or without carbohydrate attached thereto which defines a capacity of Cryptosporidium sporozoites and merozoites to infect and develop in host cells.

"Cryptopain DNA" means the sequence of 1203 polydeoxyribo nucleotides identified in SEQ ID NO: 1 (FIG. 2) which encodes the amino acid sequence of Cryptosporidium antigen (SEQ ID NO: 4) and any variants, mutations and fragments thereof which correspond to or would detect genes encoding the antigen and includes specific PCR oligonucleotide primers for amplification of cryptopain sequences and fragments of sequence used as genetic probes for detection of cryptopain sequence. Also included is DNA inserted into host cells for the purpose of in vivo expression of target antigen in order to stimulate the host immune system.

"Cryptopain RNA" means the sequence of 1203 nucleotides which encodes the protein sequence of cryptopain protein (SEQ ID NO: 4) (FIG. 3) and any variants, mutations and fragments thereof including polyadenylation tail which correspond to or would detect genes encoding the antigen. RNA probes and RNA inserted into host cells for the purpose of in vivo expression of target antigen in order to stimulate the host immune system are included.

"Vaccine" means protein, recombinant protein, DNA or RNA from cryptopain which, upon introduction into a host, is able to provoke an immune response including but not limited to the production of antibodies, cytokines and other cellular responses.

"Detection" means establishing or providing evidence for the presence or prior presence of living or dead Cryptosporidium by detecting cryptopain protein, Cryptosporidium protein specific activity, DNA or RNA in the host, in a host tissue specimens, or in environmental samples including water, soil, food, etc.

"Diagnosis" means establishment of the presence or prior presence of Cryptosporidium infection or disease by using the cryptopain protein, Cryptosporidium protein specific activity, DNA or RNA as a component of a diagnostic assay according to the invention.

"Prevention or prophylaxis" means the immunization or vaccination of the host with a vaccine of the invention such that Cryptosporidium disease or infection does not occur.

"Treatment" means therapeutic use of any protein or antibody to inhibit Cryptosporidium infection in a host.

"Host" or "subject" means human, or animal including birds and cattle.

"Regulatory elements" means nucleotide sequences which control the expression of genes they regulate, typically by interaction with other macromolecular species such as protein.

"Active immunity to infection" means ability of the organism to produce specific responses such as production of cytokines, lymphokines, antibodies or other substances, or cellular capacity to inhibit or retard infection in response to a contact with antigen.

"Passive immunity to infection" means the transfer to a host of the specific antibodies or other substances or cells capable of inhibiting or retarding infection.

"Cryptosporidium species" means any organism belonging to the genus Cryptosporidium, such as, for example, *Cryptosporidium parvum* or *Cryptosporidium muris*, but also includes currently less well characterized other organisms such as, for example, Cyclospora and similar organisms, such as Eimeria. Cryptosporidium species comprise Apicomplexan parasites which primarily invade cells of gastrointestinal tract and cause disease in a susceptible host.

"Recombinant vaccines" means DNA/RNA/protein segments propagated or expressed in foreign system. This includes all vaccines other than biologically derived vaccines.

"Biologically derived vaccines" means vaccines made from a protein or carbohydrate generated in the organism of origin.

DETAILED DESCRIPTION OF THE INVENTION

The current invention is based on findings that cryptopain, a cathepsin L-like cysteine proteinase, localized at the Cryptosporidium sporozoites surface or within its cell, is involved in Cryptosporidium infectivity and that such infectivity can be prevented by cryptopain inhibitors.

Cryptopain deduced amino acid sequence shows homology to other cathepsin L-like cysteine proteinases indicating that the mature active enzyme is a 25 kDa protein of 225 amino acids. Cryptopain DNA has been isolated, purified, sequenced and recombinantly produced. Cryptopain fusion protein in which the fusion partner is thioredoxin has also been recombinantly produced.

Due to its unique biological activity, cryptopain may be advantageously used for prophylactic, therapeutic, diagnostic and detection purposes.

This invention, therefore, relates to isolated native and recombinantly produced cryptopain; cryptopain amino acid, DNA and RNA sequences; and to vaccines, antibodies, proteins and synthetic proteins, DNAs and RNAs useful for prophylaxis, treatment, diagnosis and detection of infections caused by any Cryptosporidium organism or any organism belonging to Cryptosporidium species.

More specifically, the invention concerns identification of cryptopain a Cryptosporidium antigen cryptopain comprised of a protein or polypeptide, identification of DNA of the Cryptosporidium antigen gene within the locus, sequencing DNA encoding the Cryptosporidium antigen, expressing portions of the locus encoding the Cryptosporidium antigen and using the expressed antigens for preparation of vaccines or for preparation of polyclonal or monoclonal antibodies.

I. Cryptopain—*Cryptosporidium Parvum* Antigen

Cryptopain is cathepsin L-like cysteine proteinase. It is structurally and functionally similar to other cysteine proteinases, represented, for example, by Carica papain and *Plasmodium vinckei* cysteine proteinase, and its activity is inhibited by group of cysteine proteinase specific inhibitors.

A. Cysteine Proteinases—Their Function Structure and Inhibition

There are four major classes of proteinases for which the catalytic mechanism has been defined. These proteinases are designated cysteine, aspartic, metallo and serine proteinases. The major mammalian cysteine proteinases are the lysosomal cysteine proteinases, cathepsins B, H and L proteinases and the cytoplasmic calpains. Mammalian cysteine proteinases B and L are also active at neutral pH, and are found outside the cell and may function in the degradation of extracellular proteins. The sequences of the protozoan cysteine proteinases identified to date show that they are more closely related to cathepsin L than to cathepsin B. Cysteine proteinases essentially contain amino acids cysteine, histidine and asparagine which are important for the action of the proteinases. The sulfonium ion of the cysteine provides the nucleophilic attack on the carbonyl group of the targeted peptide bond in order to effect hydrolysis of the bond.

Calpains and cathepsins are generally distinguished from each other by their cellular locations and by their inhibition profile. For example, cathepsins, but not calpains, are inhibited by the peptidyl diazomethane and peptidyl fluoromethylketone inhibitors Z-phe-ala-CHN$_2$ (diazomethane) and Z-phe-ala-FMK (fluoromethylketone). Both lysosomal cysteine proteinases and calpains are inhibited by the class-specific inhibitor E64 and the more general inhibitor leupeptin.

Peptide inhibitors have been used to determine the peptide bond specificity of proteinases. The specificity of the inhibitor is determined by the amino acid residues, for example, phe-ala residues, which bind in the pocket formed by the active sites of the enzyme. Peptide inhibitors only bind to active enzyme, i.e. enzyme which has a conformationally correct enzyme pocket. Peptide inhibitors are useful for detection of the presence of specific types of cysteine proteinases in living systems as they may allow the localization or detection of enzymatic activity in the absence of isolation and purification of the enzyme with the subsequent development of antibody probes. Since isolation of active enzyme by biochemical techniques requires large amounts of material and the isolated enzyme is often not stable, use of peptide inhibitors instead is very advantageous.

Proteinase inhibitors are a new type of agent for treatment of protozoan infection. Cloning of genes for selected proteinases, expression of the proteinases, and molecular modeling of the proteinases are techniques which have facilitated the development of cysteine proteinases inhibitors specific for a given enzyme, such as for example, falcipain of *P. falciparum*. In addition, the differences between mammalian and protozoan cysteine proteinases and between cysteine proteinases of specific protozoa allow development of detection techniques for the organism based on the acting of the enzyme, DNA, RNA and antibodies.

B. Cryptopain Gene Cloning, Sequencing and Genomic Southern Analysis

In order to provide consistently the same antigen for production of antibodies or vaccines, and for recombinant production of fusion proteins and other agents useful for prophylactic therapeutic and diagnostic purposes, cryptopain was cloned, sequenced and genomic Southern analysis was performed to determine whether there was one or more cysteine proteinase similar to cryptopain.

Degenerative oligonucleotides were synthesized from the sequences encoding the active sites of papain like cysteine proteinases centered around the active site cysteine and histidine as seen in FIG. 1 and around the active site arginine described in Example 2. In FIG. 1, the primary structures of cysteine proteinases for *L. mexicana, T. brucei*, and human cathepsin-L are compared to the primary structure of *C. parvum* cryptopain. The diagram in FIG. 1 shows the conserved cysteine and histidine residues involved in the active site, and the cysteine residues apparently involved in disulfide bridges. For cryptopain, the conserved cysteine is C-24, the conserved histidine is H-164. The proposed disulfide bridges are 21–65, 56–103 and 158–210. FIG. 1 is a modified FIG. 19.4, from *Biochemical Protozooloqy*, 214, Ed. G. Coombs, et al., Tayla and Francis, London (1991).

For fragment amplification, a number of oligonucleotides were tried without success until oligonucleotides specific for the *Plasmodium vinckei* cysteine proteinase, described in Example 2 were identified. These oligonucleotides were found to be suitable for and were therefore used to amplify a fragment of genomic DNA from Iowa isolate *Cryptosporidium parvum* oocysts.

The fragment was sequenced using methods described below and known in the art and found to encode a 459 bp portion of a cysteine proteinase gene seen in FIG. 2, DNA residues 869–1326. The fragment was hybridized to an Iowa isolate genomic Southern blot which indicated that the cysteine proteinase was a single copy gene. Results are seen in FIG. 5.

Figure 5:
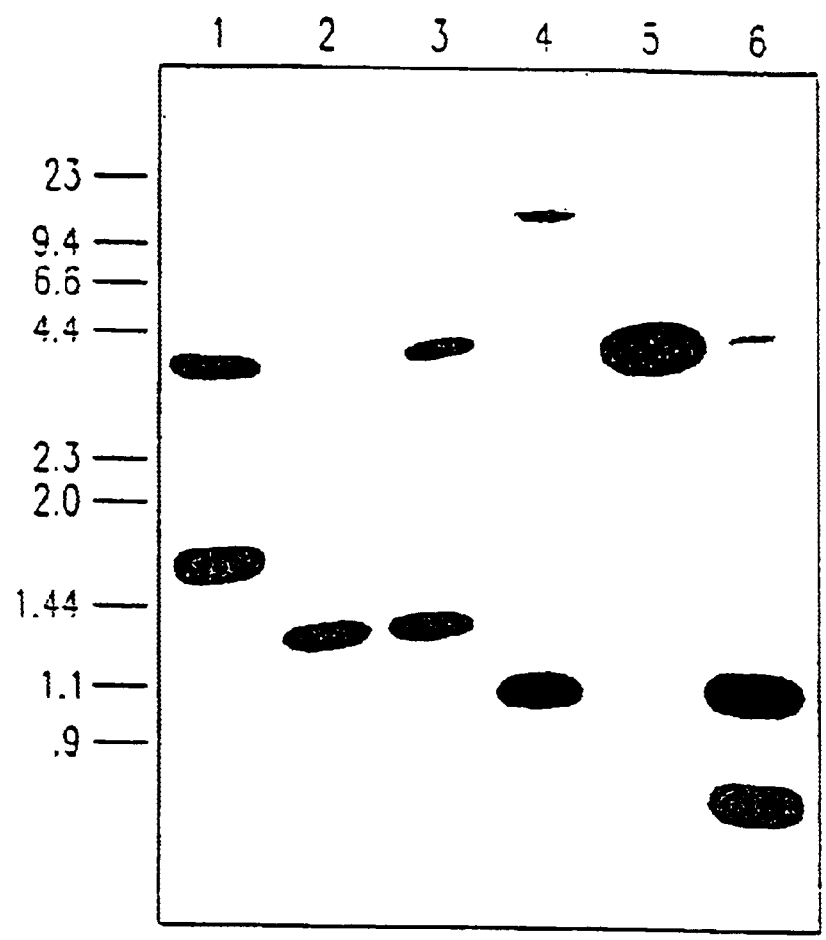
FIG. 5 shows a genomic Southern analysis of Cryptosporidium DNA using the cryptopain probe.

FIG. 5 is a genomic Southern analysis of Cryptosporidium DNA using the cryptopain probe. In FIG. 5, lane 1, the probe hybridizes to two Hind III fragments. These fragments are of approximate size 1.5 and 4 kb. In lane 2, the probe hybridizes with a Hae III fragment of 1.2 kb. In lane III the probe hybridizes to fragments of 1.2 and 4 kb of a Hind III/Hae III digest. In lane 4, the probe identifies fragments of 10 and 1 kb in an NsiI digest. In lane 5, the probe identifies a single band of 4 kb in an ScrII digest and in lane 6 it identifies fragments of 1.0, .5 and 4 kb in an NsiI/ScrII digests. The presence of 1 or 2 bands greater than the size of the probe in all digests indicates that the cysteine proteinase is a single copy gene.

The 459 bp Iowa fragment was then used to identify naturally infected neonatal calf (NINC) according to *Infect. Immun.*, 61:40 (1993) library clone which encoded the entire gene and 5' and 3' flanking regions. The sequence of this clone appears in FIG. 2 and is identified as (SEQ ID NO: 1). The sequence of the open reading frame was determined.

The corresponding sequences of the NINC clone and the 459 bp sequence of the Iowa cysteine proteinase isolate are identical indicating that cryptopain is highly conserved in these isolates and that its function is essential for Cryptosporidium.

Sequences identified as SEQ ID NOs: 1–6 disclosed in this invention are new. These sequences represent nucleotides and amino acid sequences of *C. parvum* antigen. They were prepared according to methods described in Examples 1, 2 and 3.

SEQ ID NO: 1 is the DNA sequence of the Cryptosporidium cryptopain. The sequence (SEQ ID NO: 1) comprises 1663 base pairs and comprises 5' and 3' flanking sequences, pre, pro (SEQ ID NO: 2) and mature enzyme (SEQ ID NO: 3) sequences.

SEQ ID NO: 4 is the amino acid sequence of the cryptopain. The cryptopain contains 401 amino acids and contains pre and pro fragments (SEQ ID NO: 5), and mature enzyme (SEQ ID NO: 6).

Sequences 7–8 are known and correspond to cysteine proteinases isolated from other organisms, namely from Carica and *P. vinckei*. Homology between these and the current *C. parvum* cysteine proteinase is shown and described in FIGS. 1 and 4.

Sequences identified as SEQ ID NOs: 9–12 are primer sequences.

Sequences SEQ ID NOs: 13–15 represent amino acid fragments of cryptopain.

Sequence SEQ ID NO: 16 represents a 1206 fragment of cryptopain DNA.

C. Structure of the Cryptopain Gene and its Encoded Protein

The function of cryptopain is highly correlated with the structure of the protein which is determined by the corresponding sequence. In addition, regulation of the function is, at least in part, dependent upon the presence of the pro sequence.

Sequence identified as SEQ ID NO: 1 (FIG. 2) is a DNA sequence of cryptopain. Sequence identified as SEQ ID NO: 4 (FIG. 3) is its corresponding protein. Search of the Gene Bank and Swiss Protein Bank revealed that these sequences were highly homologous to cathepsin L-like sequences of various organisms as seen in FIG. 4.

FIG. 4 is an amino acid alignment showing marked amino acid similarities of cryptopain of Cryptosporidium (SEQ ID NO: 4) cysteine proteinase (papain) of Carica (SEQ ID NO: 7) and mature cysteine proteinase *Plasmodium vinckei* (SEQ ID NO: 8). In FIG. 4, the mature enzyme of *P. vinckei* and the pre pro enzymes of cryptopain and papain (Carica) are lined up.

The active site cysteine shown at site 200 is embedded in a 7 amino acid fragment CGSCWAF (SEQ ID NO: 13) which is conserved in all three enzymes and was one of the sites chosen to make degenerate oligonucleotides primers listed in FIG. 7A. There is not a high degree of conservation of sequence between the 3 enzymes around the active site histidine seen at 341. However, the conserved arginine at 392 is embedded in an amino acid fragment YWL/IVRNSW (SEQ ID NO: 14) which only differs by 1 amino acid in *P. vinckei* cysteine proteinase and cryptopain. This substitution of I and L was not engineered into the degeneracy of the *P. vinckei* oligonucleotide. Nonetheless, the degenerate oligonucleotide 782 containing sequence for VRNFW (SEQ ID NO: 15) and the active site cysteine oligonucleotide 781 were specific enough to amplify the 459 bp fragment. Unlike cryptopain, the *P. vinckei* has a large insertion seen in amino acids 358–386 between the conserved cysteine and arginine that were the basis for nucleotide PCR of the 459 bp *C. parvum* fragment.

D. Production of Cryptopain Recombinant Protein

Recombinant cryptopain proteins are useful as antigens for preparing antibodies which will inactivate cysteine proteinase and provide antibody probes to detect the presence of the organism in the environmental and clinical diagnostic setting. Their recombinant production is therefore important.

Recombinant proteins of the invention were produced as described in Example 5. Generally, the 1203 bp cryptopain open reading frame (ORF) is engineered for in frame expression as a thioredoxin fusion protein in the Invitrogen vector pTrxFus, or any other suitable vector seen diagrammed in FIG. 8. This vector is used to create C-terminal fusions to *E. coli* thioredoxin. There is a multiple cloning site which allows in frame fusion of foreign protein with thioredoxin. Between the thioredoxin and the foreign protein there is an enterokinase cleavage site. Enterokinase treatment permits the release of thioredoxin from the protein. pTrxFus DNA is digested with for example KpNI and XbaI and the intervening fragment is removed for example, by gel purification.

Primers 7B1 and 7B2 were used to amplify the pre pro enzyme sequence from Iowa Cryptosporidium DNA. The primer 7B1 has a KpNl site and the primer 7B2 has an XbaI site engineered into the 5' end of the oligonucleotides. These enzymes are used to digest the amplified DNA so that it could be inserted directionally and in frame into the KpnI/XbaI restriction digested pTrxFus. Then, the vector, such as pTrxFus, containing the sequence for the pre pro enzyme, is used to transform competent *E. coli* cells. Ampicillin resistant transformants are then analyzed for plasmid DNA by restriction with KpNI-XbaI and by sequence for the presence, orientation and reading frame of the gene. Clones containing the same gene are induced for expression of cryptopain and expression of the fusion protein, such as for example cryptopain-thioredoxin, at 57 kD, was analyzed by SDS-PAGE as seen in FIG. 9, followed by immunoblot with antithioredoxin antibody. Conditions for optimal production of soluble protein in *E. coli* are assessed.

Results of the actual preparation of recombinant cryptopain using vector pTrxFus are seen in FIG. 9. FIG. 9 shows proteins harvested from a lysed cell culture, i.e., the soluble supernatant proteins. Lane 1 is wild type thioredoxin. Lanes 2, 3 and 4 are thioredoxin cryptopains harvested from cell culture at 2, 3 and 4 hours of growth of thioredoxin cryptopain. The pellet fraction showed no fusion protein indicating that the cryptopain-thioredoxin is wholly soluble. Growth was maximal at 3 hours and degradation products of Mr less than 57 were visible at 4 hours indicating that the optional time for harvesting culture was around 3 hours.

Fusion protein may be purified by osmotic shock or heat treatment of cell lysates to produce highly purified fusion protein. The fusion protein is advantageously cleaved with enterokinase at a cleavage site comprising 4 asparagine and 1 lysine sequence.

Production of cryptopain may be accomplished in multiple procaryotic or eukaryotic cells, including baculovirus, insect cells, yeast and mammalian cells. Cryptopain is purified by any suitable method known in the art, such as incorporation of histidine and purification by nickel chromatography, heat treatment of fluoredoxin fusion protein with subsequent harvesting of soluble protein.

I. Inhibition of Sporozoite Invasion

In order to determine whether the invasion of Cryptosporidium sporozoites may be inhibited, active site inhibitors of cathepsin L-like cysteine proteinases were investigated.

Cryptosporidiosis infection is caused by the invasion of cells with Cryptosporidium, typically *Cryptosporidium parvum*. In order to provide prophylactic, therapeutic, diagnostic or detection agents, it is necessary to determine what the function of cryptopain in the process of cell invasion is, and whether or not during the Cryptosporidium cell invasion cryptopain acts at the surface of the sporozoites. For this reason, studies were performed using known inhibitors to determine entry of the sporozoites into the cells.

Because the sequence of cryptopain (SEQ ID NO: 4) had high homology with other cysteine proteinases, and has an N-terminal hydrophobic region, it was decided to determine if *C. parvum* secreted cysteine proteinase. The biotin modification of phe-ala-fluoromethylketone (BPAFMK) makes it unable to enter intact cells. Therefore, the biotinylated phe-ala fluoromethylketone was used to determine whether a cathepsin-L like cysteine proteinase was active either at the surface of the Cryptosporidium sporozoites or in the supernatant media during invasion of Madin Darby canine kidney (MDCK) host cells and whether it allows *C. parvum* to enter the cells. Results are seen in FIG. 10.

FIG. 10A shows the % of sporozoites invasion as a function of the concentration of three cysteine proteinase inhibitors, namely inhibitors trans-epoxysuccinyl-L-leucylamido-(4-guanidino) butane (E64), obtained from Sigma, St. Louis, BPAFMK, obtained from Enzyme Systems, Dublin, Calif. and K-III, research drug of Arris Pharmaceutical, South San Francisco, Calif. The inhibitors were administered within the range of $10^{-3}$ to $10^{1}$ (0.001 to 10 mM).

As seen in FIG. 10, one hundred nM of all three inhibitors decreased invasion by Cryptosporidium to 20–30% of untreated controls. The inhibition of invasion of sporozoites by BPAFMK (FIG. 10) shows that cryptopain is involved in a proteolytic events which are necessary for invasion and intracellular development of Cryptosporidium. Results seen in FIG. 10 therefore show that cryptopain is either localized at the surface of the Cryptosporidium sporozoites, is a part of the sporozoites membrane or is localized internally and is released during the invasion of the host cell.

Assessment of other studied cysteine proteinase inhibitors (E64 and K-III) which were not chemically modified to prevent entry into the cell indicate that there is more than one cathepsin-L-like cysteine proteinase inhibitor which will prevent invasion and intracellular development.

Although not listed here, it is to be understood that other cysteine proteinase inhibitors, as long as these inhibitors inhibit Cryptosporidium invasion, are intended to be within the scope of this invention. The examples of active site inhibitors are trans-epoxysuccinyl-L-leucylamido-(4-quanidino) butane (E64), fluoromethylketone, diazomethanes, vinyl sulfones and cystatins.

Another class of inhibitors derived from pro region of cryptopain and its derivatives change the active enzyme into a proenzyme.

As described above, the complete DNA and amino acids structures of cryptopain (SEQ ID NOs: 1 and 4) comprise pre, pro and mature enzyme (SEQ ID Nos: 2 and 5) sequences (SEQ ID NOs: 3 and 6), delineated in FIG. 1 and in FIG. 4. These pre, pro and mature regions or elements are identified on the basis of homology to previously discovered and investigated cysteine proteinases, seen in FIG. 1, compared to *Cryptosporidium parvum* cryptopain. *Biochemical Protozoology*, (supra). The N-terminus of the cryptopain sequence contains pre pro sequence (SEQ ID NO: 2). The cryptopain pre sequence is predicted by Kyto-Doolittle hydropathy plot seen in FIG. 6 to contain a hydrophobic sequence. Such sequences typically target the protein to a membrane.

Inactive cysteine proteinases are called proenzymes. Proenzymes of cysteine proteinases consist of at least a pro amino acid sequence which interacts conformationally with the contiguous mature enzyme sequence to render it inactive until the pro sequence is cleaved releasing the active mature enzyme. Recent evidence indicates that the pro sequences of cysteine proteinases are excellent specific inhibitors of their respective mature active enzymes (*Protein Eng.*, 8:59 (1995)).

Thus, the pro sequence (SEQ ID NO: 5) of cryptopain is a good candidate and may be produced by recombinant or synthetic means for use as a pharmacological agent to prevent cryptosporidium infection and/or the consequences of infection.

III. Prophylaxis or Treatment Via Passive or Active Immunization

For protection and treatment of human or animal subjects subjected to exposure to Cryptosporidium, or subjects already suffering from Cryptosporidium infection, both passive or active immunization using the cryptopain antigen is appropriate.

Surface active enzymes with confirmed essential functions for the parasite infectivity, like cryptopain, are targets for passive or active immunization. Cryptopain binds to antibodies which specifically bind to epitopes of Cryptosporidium which are recognized by B and T cells.

For prophylactic, therapeutic or diagnostic purposes, the proteins of the invention are produced in large amounts by inserting the *Cryptosporidium parvum* DNA, described above, into an expression vector such as pGEX, pET-9d, pTrxFus or baculovirus obtained from Invitrogen. The thus constructed hybrid vector is then used to transform or transfect a host. The host cells carrying the hybrid vector are then grown in a nutrient medium to allow the production of the gene product.

A number of transfer vectors are available for the production of protein from both full length and partial CDNA and genomic clones. Fused or non-fused protein products, depending on the vector used, constitute up to 50% of the total protein produced in infected cells. The thus obtained recombinant proteins are frequently immunologically and functionally similar to the corresponding endogenous proteins.

The obtained polypeptide is purified by methods known in the art or described in Examples. The degree of purification varies depending on the use of the polypeptide. For use in eliciting polyclonal antibodies, the degree of purity may not need to be very high. However, as in some cases impurities may cause adverse reactions, purity of 90–95% is typically preferred and in some instances even required. For the preparation of a pharmaceutical composition, however, the degree of purity must be high, as is known in the art.

When in a therapeutic composition, the polypeptide is combined with appropriate pharmaceutically acceptable excipients adjuvants and used for the immunization of immunocompetent patients who are at risk for cryptosporidiosis either at the time of immunization or in the future.

This group includes, but is not restricted to, HIV positive individuals who are still able to respond to vaccination, animal workers, health care workers, day care center children and their caretakers, and children in the developing world.

A. Antibodies and their Production

A polyclonal or monoclonal antibody to native or recombinant protein of the invention are useful in diagnosing and detecting Cryptosporidium as well as for treatment by providing a protection against the Cryptosporidium infections.

Anti-Cryptosporidium polyclonal antibodies recognizing the cloned polypeptide are preferred over a monoclonal antibody (MAb) because they recognize multiple epitopes on the target polypeptide.

According to the method of the current invention, large amounts of recombinant cryptopain are produced by scale up processes in commercial plants which enables production of a corresponding large quantity of polyclonal antibodies or and immunogen for active immunization. The antibodies to recombinant expressed protein can also be produced according to the invention using the standard method available for production of the antibodies to native protein.

Cryptopain comprising epitopes of Cryptosporidium that is recognized by intact B and/or T cells is produced in large amounts as described above and in Examples, purified and used to detect or characterize anti-*Cryptosporidium parvum* antibody in the body substances of populations at risk of prior or current cryptosporidial infection. Cryptopain is also used for immunization. Typical intramuscular immunization schedules are as follows.

Cryptopain plus equal volume complete pharmaceutically acceptable adjuvants and excipients is used at the beginning of immunization. Antigen plus equal volume incomplete adjuvant is used at week 2. Antigen plus equal volume incomplete adjuvant at week 4.

In addition, antibodies to such antigens are obtained by immunizing animals, such as rabbits or goats, with the polypeptide plus adjuvant, as described above.

The antibodies of the invention are also used to detect Cryptosporidium antigens in body substances, for example, stools of populations at risk of cryptosporidial infection by, e.g., collecting stool samples (*Manual of Clinical*

*Microbiology*, 1986, supra), mixing with Streather's solution 1:4, and incubating with antibody followed by addition of a fluorescein conjugated second antibody. In alternative, calorimetric labeling which do not require special microscope equipment or other detection methods also suitable.

B. Biologically Derived or Recombinant Anti-Cryptosporidium Vaccines

Vaccine is a biologically derived or recombinantly prepared agent useful for artificially acquired immunization in a host. The current invention describes a production and provides biologically derived and recombinant vaccines for active immunization of animals and humans against cryptosporidiosis and for the preparation of passive immune products for treatment of the established infection.

The scope of the invention is, therefore, intended to include both biologically derived or recombinantly prepared vaccines based on the antigens of the invention.

A recombinant vaccine is produced by identifying the relevant antigen or antigens of Cryptosporidium species, cloning them and expressing them using suitable vectors. This approach yields immunogens which are reproducible in sufficiently large quantities to allow preparation of vaccine for active immunization. Recombinant vaccines are useful for immunization of the potential Cryptosporidium host, such as for example for inoculation of cows, and to produce the host's own antibodies against Cryptosporidium infection.

Additionally, the recombinant vaccines may be used for production of passive immunotherapeutic agents. For example, when the cow is inoculated with the vaccine it begins to produce hyperimmune colostrum. Hyperimmune colostrum from the immunized cows is then purified to yield Ig for passive immunotherapy of immunocompromised persons, primarily AIDS patients, children, etc.

These vaccines are also useful for widespread use in calves to provide a primary protection against Cryptosporidium infection. Providing the herd with anti-Cryptosporidium immunity decreases the risk for waterborne outbreaks of cryptosporidiosis in areas where the watershed includes dairy lands. This provides a secondary benefit to human residents of those areas.

In addition, DNA or RNA may be introduced into a host such that propagation and/or expression of the encoded protein occurs in the host utilizing a so called "foreign expression system".

Anti-Cryptosporidium vaccine of the invention contains a Cryptosporidium antigen identified by the invention, modified in such a way that it is incapable of producing the Cryptosporidium symptoms but at the same time it is capable of eliciting the production of specific protective antibodies against the disease when introduced in the body.

Protection from cryptosporidiosis appears to be due to mucosal immunity which, if absent in AIDS patients, is difficult to establish but, if present, may afford protection against clinical cryptosporidiosis as AIDS progresses.

Thus, the invention describes vaccines able to provide active B cell-immunity and potentially T cell immunity against cryptosporidiosis in normal persons, in persons at risk for AIDS or in otherwise immunocompromised patients.

C. DNA and RNA Vaccines

Recently, new approaches appeared which utilize so called DNA or RNA vaccines. These approaches are described in *Science*, 259:1745 (1993), hereby incorporated by reference.

DNA or RNA vaccines or native immunity are produced according to the methods described Ibid. Briefly, nucleic acid vectors containing cryptosporidium antigen DNA nucleic acid are injected, preferably intramuscularly to the host. The nucleic acid enters or is transmitted where it results in production of antigen. The antigen elicits immune responses. in the form of specific anti-Cryptosporidium antigen antibody or cell medicated immune events. In this way, the host receives DNA or RNA and provides his/her own humoral immunity and/or cell mediated responses.

IV. Diagnostic/Detection Utility

An important part of this invention is a method of diagnosing Cryptosporidium infection or detection of Cryptosporidium in the tissue samples or in the environment.

The diagnostic method comprises contacting a body fluid or tissue with an anti-Cryptosporidium polyclonal or monoclonal antibody having specificity for the antigen of this invention or its fragments, or vice versa, and ability to detect any selective binding of the antibody to any antigenic Cryptosporidium proteins present in the body fluid, tissue or specimen or selective binding of the antigen to the anti-Cryptosporidium antibody.

The detection of the antibody-antigen complex in body specimens or environmental samples may be conducted by any method known in the art. The detection methods include solid phase, double antibody, sandwich double antibody, and triple antibody assays, including ELISA and the like. Also suitable are enzyme-linked immunoassays and radioactively labeled assays.

Examples of body specimens are stools and other liquid or solid body output or tissue samples obtained from a subject. Examples of body fluids are blood, serum, saliva, urine, and the like. Methods for the preparation of the body substance and the body fluid are standard in the art and are described, for example in *Manual of Clinical Microbiology*, Chapter 8, "Collection, Handling and Processing of Specimens", 4th edition, Eds, Lennette, E. H., Balows, A., Hausler, W. J. and Shadorny, A. J., American Society for Microbiology, (1986)).

Diagnosis and detection methods also comprise contacting the DNA and RNA of body fluid, tissue, specimen and environmental sample with DNA and RNA of the invention or fragments thereof and the amplification of this specific interaction via PCR, branched chain nucleic acid technology and other amplification technologies such that the presence of Cryptosporidium DNA and/or RNA in the bodily fluid, tissue, specimen or environmental sample may be detected. Agents suitable for immunodiagnostic use are proteins comprising epitopes of *Cryptosporidium parvum* that are recognized by intact B and/or T cells. These proteins are produced as described above, purified and used to detect or characterize anti-*Cryptosporidium parvum* antibody in the body substances of populations at risk of prior or current cryptosporidial infection. In addition, antibodies to such proteins are obtained by immunizing animals, such as cows, rabbits or goats, or birds with the vaccine combined with an adjuvant.

Additionally, detections of Cryptosporidium may be made by determining cryptopain activity in biological or environmental samples by methods used and known in the art.

V. Immunotherapy and Prophylaxis

The immunotherapy of cryptosporidiosis in humans and animals may be conducted by administration of the antibodies of the invention to patients with cryptosporidiosis to effectively reduce their symptomatology.

A method for immunotherapeutic treatment, retardation, or inhibition of cryptosporidium infection comprises administering to a subject in need of such treatment an amount of an anti-Cryptosporidium polyclonal or monoclonal antibody prepared according to the invention, effective to provide immunity against the invasion of Cryptosporidium or effective to inhibit the existing Cryptosporidium infection.

A method of prophylaxis of Cryptosporidium infection comprises administering to a subject in need of such treatment a vaccine, as described above, comprising the protein or recombinant protein of this invention capable of endogenous development of inhibitory amount of anti-*Cryptosporidium parvum* antibodies.

Typical immunization is achieved by inoculation of the animal, bird or human host with the antigen protein combined with adjuvant.

For passive immunotherapy when used to passively immunize Cryptosporidium infected hosts, the polypeptide is first combined with appropriate adjuvants and used for the immunization of cows or other donor animals to produce antibodies which may be administered to patients with cryptosporidiosis infection, particularly to AIDS patients, and to other immunocompromised hosts. Monoclonal antibodies produced in animals, in humans "humanized" from animal sources and produced through chimeric techniques and other derivative techniques may be used for passive immunotherapy.

When in a therapeutic composition, the antigen protein is combined with appropriate adjuvants and used for the immunization of immunocompetent patients who are at risk for cryptosporidiosis either at the time of immunization of in the future. This group includes, but is not restricted to, HIV positive individuals who are still able to respond to vaccination, animal workers, health care workers, day care center children and their caretakers, and children in the developing world.

VI. Qualitative and Quantitative Detection of Cryptosporidium-formulations and Kits Formulations suitable for the administration of polypeptides and antibodies such as those described herein are known in the art. Typically, other components stimulatory of immune response as well as fillers, coloring, and the like may be added, such as pharmaceutically acceptable excipient, additives and adjuvants.

For qualitative and quantitative determination of the presence of the Cryptosporidium infection and environmental contamination, a kit for the diagnosis/detection of cryptosporidium is used. The kit comprises the polyclonal antibody or antigen of this invention and a means for detecting the complexing of the antibody with antigen. Another such kit comprises DNA/RNA of the invention for use in detecting complementary DNA/RNA of cryptopain. Another such kit comprises PCR primers for amplification of cryptopain sequences and a method of identifying them.

The kit is utilized for the detection of endogenous antibodies/antigens/DNA/RNA produced by a subject that is afflicted with cryptosporidiosis and antigens/DNA/RNA present in the environmental samples. Even at the early stages where the parasite is commencing invasion of a subject's cells, some amount of the Cryptosporidium antigen or the specific antibody may be detected in serum. The kit detects either the antigen with the polyclonal antibodies or the presence of the anti-Cryptosporidium antibody with the antigen. The complexing immunoreaction is detected by staining, radiography, immunoprecipitation or by any other means used in the art and suitable for these purposes.

In addition to the above, the kits may also comprise a control compounds, anti-antibodies, protein A/G, and the like, suitable for conducting the different assays referred to above.

The current invention provides an effective treatment and prophylaxis against the cryptosporidiosis infection and means of detection of the parasite and diagnosis of infection.

The following examples describe procedures used to prepare antigens, antibodies, vaccines and kits of the invention. They are illustrative only and any modification using methods known in the art is intended to be included. The following examples are not to be considered in any way limiting.

EXAMPLE 1

*Cryptosporidium parvum* Parasites

This example describes protocol used for isolation of *Cryptosporidium parvum* parasites from which the Cryptosporidium antigen was prepared.

Oocysts of the Iowa isolate of *Cryptosporidium parvum* were passaged through neonatal calves, (Pat Madin Pathasan, Pleasant Hill Farms, Id.). The passaged oocysts were purified and encysted for use in invasion assays. The detailed protocol for purification and encysting is described in *Infect. Immun.*, 61:4079 (1993). The described protocol was used unmodified.

For the DNA experiments described herein DNA was purified from $1 \times 10^9$ *Cryptosporidium parvum* according to *Mol. Biochen Parasitol*, 50:105–114, (1992).

EXAMPLE 2

Preparation of a *C. parvum* Cysteine Proteinase DNA Probe

This example describes procedural used for preparation of the *C. parvum* cysteine proteinase DNA probe.

Cysteine proteinases share DNA homology in the regions coding for the active site amino acids involved in proteolysis, specifically conserved C, H and N residues. This was used in choosing an appropriate oglionucleotide pairs to amplify the genomic DNA from Iowa isolate. The most suitable oligonucleotides were found to be those modeled in *Plasmodium vinckei* cysteine proteinase sequences around the conserved cysteine (C) and arginine (N) residues as indicated in FIG. 4.

Degenerate oligonucleotides for the active C and N sites of the *Plasmodium vinckei* cysteine proteinase were used to amplify a 459 bp genomic DNA fragment from Iowa isolate DNA. In the degenerate oligonucleotides a "/" indicates that the base pair on either side of the "/" could be included at that location in a triplet encoding an amino acid. (I) indicates inosine which will pair in hybridization reactions in a permissive manner. The oligonucleotides were PC4(sense) consisting of AAA-GGA-TCC-TGC/T-GGI-A/TG/CI-TGC/T-TGG-GCI-TT (SEQ ID NO: 9) encoding a BamHI site and the DNA sequence for C-G-S-C-W-A-F (SEQ ID NO: 13) and PC3 (anti-sense) consisting of the DNA sequence TTT-GAA-TTC-CCA-IG/CA/T-A/GTT-IC/TT/G-IAC/T-IAT-CCA-A/GTA (SEQ ID NO: 10) encoding an Eco RI site and the antisense for a protein sequence. The protein sequence in the sense direction is Y-W-I-V/I-K/R-N-S-W (SEQ ID NO: 14). The restriction sites were not required for the experiments described here.

As shown in FIG. 4, these oligonucleotides represented a 100% match for the seven amino acid C-G-S-C-W-A-F (SEQ ID NO: 13) sequence of C. parvum cryptopain and a 100% match for the five amino acids V-R-N-S-W (SEQ ID NO: 15) within the eight amino acid sequence surrounding the conserved N. These matches were sufficient for PCR amplification purposes.

One hundred nanograms of Iowa isolate DNA was amplified using reagents from GeneAmp (Perkin-Elmer, Foster City, Calif.) under the following conditions:

Initial denaturation was 94° C. for 2 minutes followed by 30 cycles of 94° C. for 20 seconds, 40° C. for 40 seconds and 72° C. for 1 minute.

The 459 bp amplification product was isolated, subcloned in the TA vector (TA Cloning kit, Invitrogen, San Diego, Calif.) and sequenced using the di-dioxy technique (Stategene Sequenase II Kit).

Iowa isolate sequence so obtained was found to be homologous to cysteine proteinases of a wide variety of organisms. The sequences of papain and the cysteine proteinase of P. vinckei are shown in FIG. 4.

EXAMPLE 3

Isolation, Sequencing and Analysis of a C. parvum Cysteine Proteinase Gene

This example describes isolation, sequencing and analysis of a C. parvum cysteine proteinase gene encoding C. parvum antigen.

The 459 bp amplification product obtained in Example 2, containing a portion of an Iowa isolate C. parvum cysteine proteinase gene was labeled with d-dATP$^{32}$ using random primers and Klenow fragment. The labeled 459 bp probe was used to screen a NINC, (naturally infected neonatal calf) λgt11 genomic expression library.

Three clones, designated E1.6, E4 and RCB1.2, were identified in the library and were purified to homogeneity. Two of them, E1.6 and E4, were subcloned in Bluescript for sequencing (Sequence II kit) and were found to contain the complete cryptopain sequence and 5' and 3' flanking sequences as determined by analysis of the open reading frames within the clones and Genebank Search using the deduced amino acid sequence.

The entire sequence of E1.6 is designated SEQ ID NO: 1 and includes flanking sequences 5' and 3'. The mature enzyme sequence is designated SEQ ID NO: 3.

EXAMPLE 4

Southern Hybridization

This example describes Southern hybridization method used to detect the gene of the invention in genomic DNA.

One mg of Iowa DNA was digested with the restriction enzymes, Hind III, Hae III, Nsi, Scr II and combinations thereof, according to conditions for use of each enzyme as provided by the manufacturer (Promega). Digested DNAs were subjected to electrophoresis in 0.8% agarose gels in 1X TAE. The gel was blotted to a nylon membrane Hybond N+, obtained from Amersham per manufacturer's instructions.

Results are seen in FIG. 5 which shows a generic Southern analysis using DNA cut and separated in this manner (lane 1=Hind III, lane 2=HaeIII, lane 3=HindIII/HaeIII, lane 4=NsiI, lane 5=SrcII and lane 6=Nsi/SrcII). The 459 bp probe was labeled with $^{32}$P-ATP and hybridized to the membrane.

EXAMPLE 5

Preparation of Recombinant Cryptopain

This example describes the preparation of recombinant cryptopain.

The primers 7B1 and 7B2 (FIG. 7B) were synthesized at the Biomedical Research center, University of California, San Francisco. 7B1 is a sense oligonucleotide and is comprised of a KpnI restriction enzyme recognition site at the 5' end followed by coding sequence for the 5' end of the pre pro cryptopain sequence. 7B2 is an anti-sense oligonucleotide and is comprised of an XbaI sequence at the 5' end followed by the antisense coding sequence of the 3' end of the preprocryptopain sequence. When used as a pair of PCR amplification oligonucleotides, these oligonucleotides allowed the amplification from genomic Cryptosporidium DNA of the entire cryptopain gene with KpnI and XbaI sequences at the 5' and 3' ends respectively.

The 7B1 and 7B2 sequences were designed so that after YpnI and XbaI digestion of the amplification product, the resultant fragment could be introduced in a directional manner into pTrxFus which was cut with KpnI/XbaI. Amplified and restricted DNA was visualized on a 0.8% agarose-1XTAE gel using ethidium bromide. The amplified and endonuclease restricted band was excised from the gel and purified using a glass bead technique (Gene-Clean). pTrxFus was also digested with the enzymes KpnI and XbaI, enzymes uniquely present in the sequence in the poly linker (FIG. 8), and the small intervening sequence was removed by gel purification as noted above. pTrxFus and preproc-ryptopain DNA, prepared in this manner, at 1:1 and 1:5 molar ratios were ligated overnight at 14° C. in the presence of ligation buffer and T4 DNA ligase at a concentration of 50–250 ng insert DNA/10 μl.

G1724 chemically competent cells were made as described by Xi-Lvitrogen. Three to five μl of ligation mixes and control mixes were introduced into separate tubes of competent cells and the tubes were incubated on ice for 30 minutes. Tubes were incubated in a 42° C. heating block for 90 seconds and placed on ice for 2 minutes. Eight hundred μl of room temperature of enriched tryptone containing broth medium was added to each tube and the tube was incubated with shaking at 30° C. for 60 minutes. Twenty-five and 100 μl of each transformation mix was plated on RMG-Ampicillin transformation plates and the plates were incubated at 30° C. overnight.

Nitrocellulose membrane replicas of colonies were prepared from the transformation plates, the adherent cells lysed in alkaline solution and the DNA fixed to the membranes. Nitrocellulose membranes were hybridized with probes to contain cryptopain DNA and following hybridization with a cryptopain, probe were colony purified. DNA was purified from colonies and the identity of the foreign DNA verified by restriction analysis and sequence analysis.

Purified colonies were grown in 1 μl aliquots for analysis. Growth conditions were varied with respect to time (2, 3, 4 hours) and the bacteria lysed for evaluation of soluble and insoluble proteins. Results are shown in FIG. 9.

Figure 9:
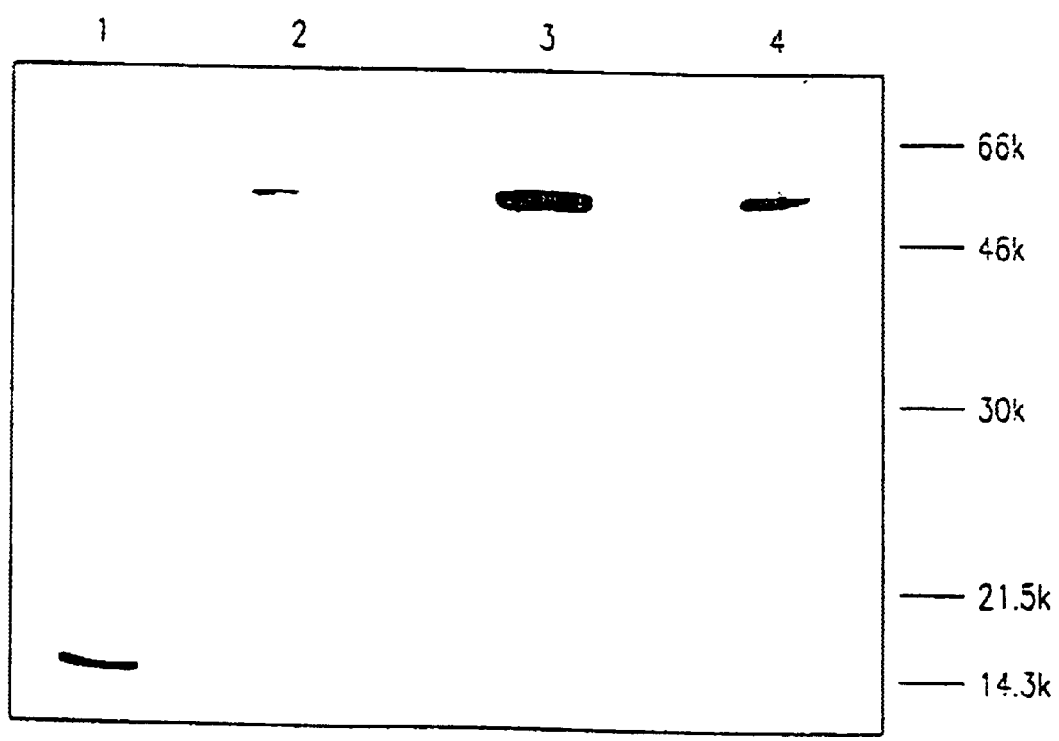
FIG. 9 is a Western blot of cryptopain expressed as a thioredoxin fusion protein and detected by anti-thioredoxin antibody.
Figure 10A:
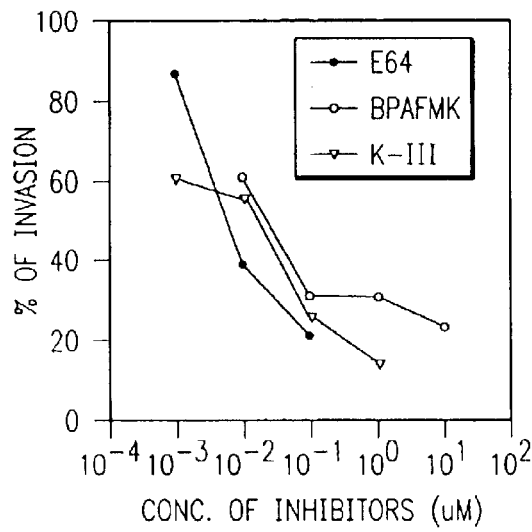
FIG. 10A is a comparative graph of three cysteine proteinase inhibitors biotinylated fluoromethylketone (BPAFMK) (FIG. 10B); trans-epoxysuccinyl-L-leucylamido-(4-guanidino) butane E64 (FIG. 10C); and proprietary compound K-111 (FIG. 10D).
Figure 10B:
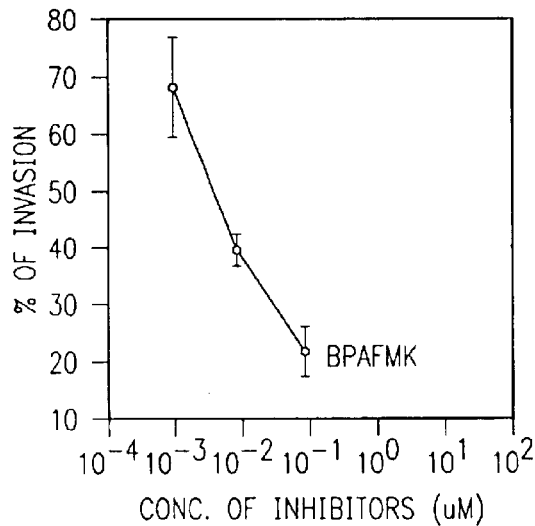
FIGS. 10B–10D show standard deviations.
Figure 10C:
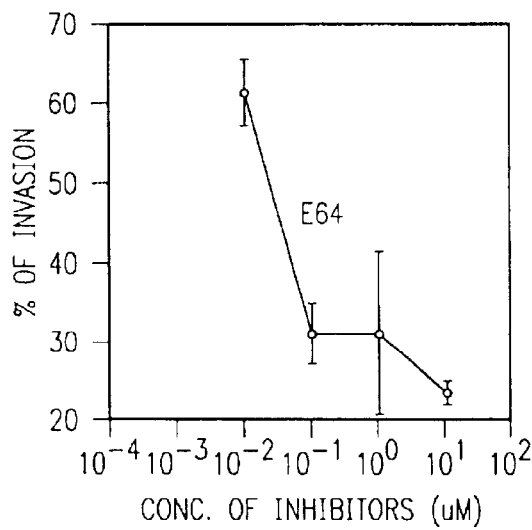
Figure 10D:
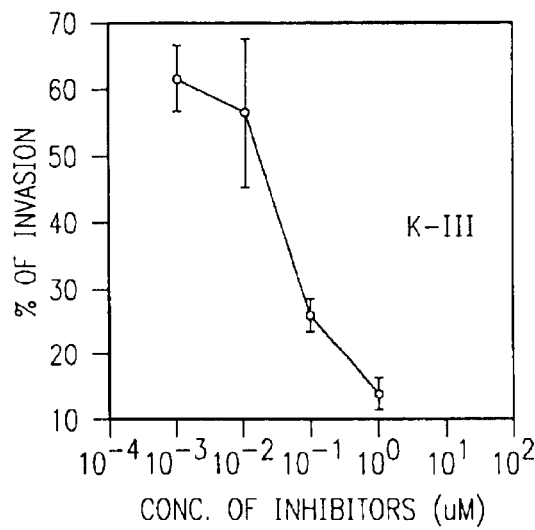

FIG. 9 shows soluble proteins from 10 μl of lysate at 2, 3, 4 hours in lanes 2, 3, and 4 on an immunoblot of an SDS-PAGE gel. Cryptopain fused to thioredoxin appears as a 57 kDa protein which is appropriate for the size of the fusion partner (12 kDa) and the size of preprocryptopain (35 kDa). Lane 1 is the thioredoxin control. All lanes are visualized with anti-thioredoxin antibody followed by chemiluminescent detection (Amersham). Yield, using this expression system, was maximal at 3 hours of bacterial growth and was estimated at 0.9 mg cryptopain-thioredoxin per 250 ml culture. Although the yield was very high in this system, purification after enterokinase removal of the fusion partner was less satisfactory.

EXAMPLE 6

Large Scale Purification of Recombinant Cryptopain

This example describes the purification procedure for cryptopain.

In order to provide large quantities of cryptopain purified from its fusion partner, thioredoxin, the KpnI/XbaI preprocryptopain DNA fragment of Example 5 was cloned into an improved vector known as pThio His (Invitrogen). The improvements of the invitrogen system were:

1) Metal binding sites were engineered into the sequence between the thioredoxin reading frame and the enterokinase recognition site facilitating large scale purification of the fusion protein over chromatography columns (Pro-bond, Invitrogen).

2) Growth of transformed bacteria (Top 10, Invitrogen) in the presence of more standard media.

3) Ability to cleave the foreign protein from the fusion partner using enterokinase while the fusion protein was on the nickel column allowing a high degree of purification from the fusion partner.

Colonies were prepared as in Example 5 using Top 10 *E. coli*. Large scale group was accomplished, the bacteria harvested and lysed and the fusion protein collected by passage over Probond or other metal chelation columns. The columns were washed with normal saline and cryptopain was collected by passing dilute enterokinase over the column.

EXAMPLE 7

Inhibition of Cryptosporidium Invasion and Intracellular Development in MDCK Cells with Inhibitors of Cathepsin-L Like Cysteine Proteinases This example describes studies performed to detect inhibition of Cryptosporidium invasion and intracellular development in vitro using cathepsin-L-cysteine proteinase inhibitors.

Cryptosporidium oocysts of the Iowa isolate were encysted according to Example 1. To assess the effect of inhibitors E64, BPAFMK and KIII on sporozoite invasion, inhibitors were incubated with viable sporozoites for 30 minutes prior to addition to monolayers of MDCK cells as described in (*J. Protozool.*, 386:556 (1991); and *Infect. Immunol.*, 61:4079 (1993).

Sporozoite invasion and intracellular development in MDCK cells was scored at 16 hours after fixation of MDCK cells in formalin and staining with Giemsa.

EXAMPLE 8

Detection of Proteinase Activity as a Measure of Viability of Cryptosporidium Organisms This example describes a method for detection of proteinase activity as a measure for viability of Cryptosporidium organism in environmental samples.

Cryptosporidium cannot be grown in culture in vitro. Available evidence indicates that acquisition of cryptosporidiosis from water, food and other environmental sites is a major source of disease spread. However, reliable methods of determining whether living Cryptosporidium species are present in a sample have not been developed.

The invention provides a method assaying activity of proteins which have a short half-life. Proteinases which are tightly regulated with respect to activation, because unrestricted activity would damage the integrity of the cell, represent one such type of proteins.

Highly specific active site inhibitors of cryptopain are used for evaluation of viability of Cryptosporidium organisms. A highly specific inhibitor of cryptopain, for example E64, KIII or pre pro cryptopain protein is labeled with a radioactive, chemiluminescent, calorimetric or other tag. The tagged inhibitor is incubated with Cryptosporidium organisms/proteins from an environmental sample and the amount of tag bound/organism relative to positive and negative control is ascertained. Number of organisms may be determined by flow cytometry.

EXAMPLE 9

Agents Suitable for Passive Immunotherapy

This example describes preparation of suitable agents for passive immuno therapy.

Recombinant cryptopain described in Example 5, or a recombinant fragment of cryptopain with or without fusion protein are used to immunize animals such as cows, goats or rabbits. The antibody developed in the body of the animal is purified from serum or milk as colostrum or used without purification for treatment of a Cryptosporidium infection of mucosal surfaces.

The antibody is delivered orally or through a tube and is optionally mixed with agents or substances which delay or prevent the inactivation of antibody in the gastrointestinal tract.

EXAMPLE 10

Agents Suitable for Active Immunotherapy

This example illustrates agents derived from *C. parvum* suitable for active immunotherapy.

Recombinant cryptopain according to Example 5, or recombinant fragments of cryptopain with or without fusion protein is used to immunize animals or humans in such a way that the animal or human develops antibody or cell mediated immune responses to Cryptosporidium which ameliorate or inhibit infection by Cryptosporidium.

EXAMPLE 11

Agents Suitable for Immunodiagnostic/ Immunodetection Use

This example illustrates procedure for obtaining agents derived from *Cryptosporidium parvum* for suitable immunodiagnostic/immunodetection use.

Recombinant cryptopain or recombinant fragments of cryptopain or antibodies (monoclonal, polyclonal or chimeric) raised to recombinant cryptopain or recombinant fragments of cryptopain are used to detect the corresponding antibody or antigen in a soluble or fixed assay.

Recombinant cryptopain is immobilized in wells and utilized to detect the corresponding antibody from humans or animals by capture of the antibody and calorimetric or other detection method.

Correspondingly, antibodies to recombinant cryptopain are immobilized in wells and utilized to detect cryptopain in secretions or feces or other bodily fluids or environmental samples. Both of these assays are also be performed in a soluble format.

EXAMPLE 12

Detection of MRNA as a Measure of Viability of Cryptosporidium Organisms

This example illustrates detection of mRNA as a measure of viability of Cryptosporidium organisms.

The presence of mRNAs which have a short half-life was assayed on the basis of the fact that many mRNAs are destroyed within 2 minutes of production and the amount of intact MRNA in a cell provides a measure of the viability of an organism.

A probe for hybridization with the MRNA of the invention is prepared and labelled with radioactive, chemiluminescent, calorimetric or other tag. The tagged probe is incubated with Cryptosporidium organisms from an environmental sample and the amount of tag bound/cell relative to positive and negative controls is ascertained. Number of organisms is determined by flow cytometry or any other suitable means.

EXAMPLE 13

Agents Suitable for Nucleotide Based Diagnosis/ Detection

This example illustrates the procedure for obtainin agents derived from *C. parvum* for nucleotides based diagnosi and/or detection.

Oligonucleotides or PCR amplification products using nucleotides derived from the cryptopain or the flanking DNA sequences is used to detect Cryptosporidium in human or animal samples or in the environment.

Oligonucleotides are used to amplify a Cryptosporidium fragment as described in the Examples above from the samples or from the environment and to detect its presence in either location. PCR amplification products or segments of DNA or RNA are used as probes to detect the presence in either location in hybridization experiments. Hybridization is either as a Southern blot or as a dot blot. The hybridization signal is amplified by a variety of techniques including the branched chain technique.

EXAMPLE 14

Preparation of Anti-cryptosporidium Vaccines

This example describes preparation of anti-Cryptosporidium vaccines using DNA, RNA or amino acid cryptopain sequences.

A vaccine for prevention and treatment of infections caused by protozoan Cryptosporidium species (Cryptosporidium) in humans and other mammals was developed by utilizing newly identified and isolated DNA and amino acid sequences of the Cryptosporidium pathogen designated cryptopain.

The antigen proteins used for preparation of vaccines correspond to cryptopain (SEQ ID NO: 4) which is identified by being a target of the polyclonal or monoclonal antibodies of the invention capable of preventing or ameliorating disease and preventing invasion and/or intracellular development in host cells.

A DNA or RNA vaccine for prevention and treatment of infections caused by protozoan Cryptosporidium species (Cryptosporidium) in humans and other mammals was developed by utilizing newly identified and isolated DNA (SEQ ID NOs: 1–3) and amino acid sequences of the Cryptosporidium pathogen designated cryptopain.

A hybrid vector comprising a DNA segment that encodes the protein antigen able to bind selectively and specifically to anti-Cryptosporidium antibodies operatively coupled to the vector was prepared and expressed as described in Example 5. This includes preparation of recombinant vaccines using the viral expression vector according to Example 5 outside of the host body but also includes preparation of DNA vaccines and procaryotic or eukaryotic host carrying the hybrid vector which may be introduced into the host vertebrate or a direct introduction of DNA or RNA into host cells generating the hosts own expression or translation of DNA or RNA to produce proteins eliciting appropriate antibodies.

EXAMPLE 15

Preparation of Anti-*Cryptosporidium parvum* Vaccine

This example illustrates procedure for preparation of anti-Cryptosporidium parvum vaccine of the invention and its use.

Vaccines use of recombinant Cryptosporidium antigens prepared according to Examples 5 and 14.

(1) Antigens

Preferably 10–200 µg of recombinant antigen of the invention, either alone or in combination is sued for preparation of the vaccine.

(2) Adjuvant

Any one of a number of adjuvants designed to either:

(a) stimulate mucosal immunity; or (b) target mucosal lymphoid tissue is sued for preparation of the vaccine of the invention.

Examples of these adjuvants are: liposomes, saponins, lectins, cholera toxin B subunit, *E. coli* labile toxin (LT) B subunit, pluronic block copolymers, hydroxyapatite, plant glucans, acetyl mannan (from Aloe Vera), aluminum hydroxide.

(3) Route of Administration

Since the vaccine must stimulate mucosal immunity, it preferably is delivered to a mucosal site.

Feasible routes of administration include: oral, nasal, rectal, and vaginal. However, boosting may occur via another route.

(4) Volume

The volume of the vaccine, while not particularly important, should be in the range that would permit ease of use. Preferred range would be about 0.5 ml–2.5 ml, including adjuvant, per one vaccine dose.

(5) Boost Schedule

Since this vaccine would be intended for immunocompromised individuals, one would expect the diminishing immune status to require a more aggressive boosting schedule than would otherwise be necessary.

The vaccine is administered to high risk patients initially when their immune status is reasonably good (i.e., CD4 count of >500). Booster schedules are typically given initially at 1 month after the primary immunization, and again every 3–4 months during progression of the immunodeficient state.

What is claimed is:

1. An isolated antibody produced against and binding to an antigen consisting of the amino acid sequence shown as SEQ ID NO:5.

2. An isolated polyclonal anti-cryptopain antibody suitable for treatment of Cryptosporidium infections wherein said antibody is administered to a person in need of such treatment, said antibody produced against and binding to an antigen consisting of the amino acid sequence shown as SEQ ID NO:5, wherein said antibody is administered in an amount effective to provide passive immunity or to inhibit existing Cryptosporidium infection.

* * * * *

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
       (A) LENGTH: 1663 base pairs
       (B) TYPE: nucleic acid
       (C) STRANDEDNESS: double
       (D) TOPOLOGY: linear (ii) MOLECULE TYPE: DNA (vi) ORIGINAL SOURCE:
        (A) ORGANISM: Cryptosporidium parvum (xi) SEQUENCE DESCRIPTION: SEQ ID NO: 1:

```
CAAAACTTCC TAATTTCTCA ATGTATTACT AATTAATAGA AAGTTTGTTT TATTTTCATG      60

TGGATAAATG AATTATTTTC TCTATACCGG CATTTGCATG CAATTTTGTA TGACTAAAAT     120

GTAAATAATT ATTTGCATGC AATTATGTGG GCATGTCATA GTTTTTCAAG AATAATAATA     180

AGATGACATG ACAAGATATT CAAAAAAATT TGATGATTAT ATGTTGAAGT TAATTGAACT     240

AAAAAGTAAT TAAGTAAAAT GGACATAGGA AACAACGTGG AAGAACATCA GGAATATATT     300

TCTGGACCAT ACATTGCATT AATTAATGGC ACTAATCAAC AAAGGGAACC GAATAAAAAG     360

TTGAAAAACA TAATAATTGC AACGTTGATT GCAATCTTTA TAGTTTTGGT TGTTACTGTA     420

TCTTTGTATA TTACTAATAA CACCAGTGAC AAAATTGACG ATTTCGTACC TGGTGATTAT     480

GTTGATCCAG CAACTAGGGA GTATAGAAAG AGTTTTGAGG AGTTCAAAAA GAAATACCAC     540

AAAGTATATA GCTCTATGGA GGAGGAAAAT CAAAGATTTG AAATTTATAA GCAAATATG      600

AACTTTATTA AAACAACAAA TAGCCAAGGA TTCAGTTATG TGTTAGAAAT GAATGAATTT     660

GGTGATTTGT CGAAAGAAGA GTTTATGGCA AGATTCACAG GATATATAAA AGATTCCAAA     720

GATGATGAAA GGGTATTTAA GTCAAGTAGA GTCTCAGCAA GCGAATCAGA AGAGGAATTT     780

GTTCCCCCAA ATTCTATTAA TTGGGTGGAA GCTGGATGCG TGAACCCAAT AAGAAATCAA     840

AAGAATTGTG GGTCATGTTG GGCTTTCTCT GCTGTTGCAG CTTTGGAGGG AGCAACGTGT     900

GCTCAAACAA ACCGAGGATT ACCAAGCTTG AGTGAACAGC AATTTGTTGA TTGCAGTAAA     960

CAAAATGGCA ACTTTGGATG TGATGGAGGA ACAATGGGAT TGGCTTTTCA GTATGCAATT    1020

AAGAACAAAT ATTTATGTAC TAATGATGAT TACCCTTACT TTGCTGAGGA AAAAACATGT    1080

ATGGATTCAT TTTGCGAGAA TTATATAGAG ATTCCTGTAA AAGCCTACAA ATATGTATTT    1140

CCGAGAAATA TTAATGCATT AAAGACTGCT TTGGCTAAGT ATGGACCAAT TCAGTTGCA     1200

ATTCAGGCCG ATCAAACCCC TTTCCAGTTT TATAAAAGTG GAGTATTCGA TGCTCCTTGT    1260

GGAACCAAGG TTAATCATGG AGTTGTTCTA GTTGAATATG ATATGGATGA AGATACTAAT    1320

AAAGAATATT GGCTAGTAAG AAATAGCTGG GGTGAAGCGT GGGGAGAGAA AGGATACATC    1380

AAACTAGCTC TTCATTCTGG AAAGAAGGGA ACATGTGGTA TATTGGTTGA GCCAGTGTAT    1440

CCAGTGATTA ATCAATCAAT ATAAGCATTT CAGTGTTTGA CTAAGTAATT CTAATATATT    1500

TCAGCATTCT CAGAGATAAT TTTAGTTCAA ATGAACAATC TATTCATATA TATAAGCATT    1560

CCATACTTAA TTATTTATTG ATTTAATAAA AATGTTTGGC TAAAGAAAGC AATCAAGATA    1620

ATTTATGGAC GTTCTATTGT TCTTACTTCA ATAATAATCC TTT                      1663
```

(2) INFORMATION FOR SEQ ID NO: 2:

(i) SEQUENCE CHARACTERISTICS:
        (A) LENGTH: 534 base pairs
        (B) TYPE: nucleic acid
        (C) STRANDEDNESS: double
        (D) TOPOLOGY: linear (ii) MOLECULE TYPE: DNA (vi) ORIGINAL SOURCE:
        (A) ORGANISM: Cryptosporidium parvum (xi) SEQUENCE DESCRIPTION: SEQ ID NO: 2:

```
TTAAGTAAAA TGGACATAGG AAACAACGTG GAAGAACATC AGGAATATAT TTCTGGACCA    60

TACATTGCAT TAATTAATGG CACTAATCAA CAAAGGGAAC CGAATAAAAA GTTGAAAAAC   120

ATAATAATTG CAACGTTGAT TGCAATCTTT ATAGTTTTGG TTGTTACTGT ATCTTTGTAT   180

ATTACTAATA ACACCAGTGA CAAAATTGAC GATTTCGTAC CTGGTGATTA TGTTGATCCA   240

GCAACTAGGG AGTATAGAAA GAGTTTTGAG GAGTTCAAAA AGAAATACCA CAAAGTATAT   300

AGCTCTATGG AGGAGGAAAA TCAAAGATTT GAAATTTATA AGCAAAATAT GAACTTTATT   360

AAAACAACAA ATAGCCAAGG ATTCAGTTAT GTGTTAGAAA TGAATGAATT TGGTGATTTG   420

TCGAAAGAAG AGTTTATGGC AAGATTCACA GGATATATAA AAGATTCCAA AGATGATGAA   480

AGGGTATTTA AGTCAAGTAG AGTCTCAGCA AGCGAATCAG AAGAGGAATT TGTT         534
```

(2) INFORMATION FOR SEQ ID NO: 3:

(i) SEQUENCE CHARACTERISTICS:
        (A) LENGTH: 678 base pairs
        (B) TYPE: nucleic acid
        (C) STRANDEDNESS: single
        (D) TOPOLOGY: linear (ii) MOLECULE TYPE: DNA (vi) ORIGINAL SOURCE:
        (A) ORGANISM: Cryptosporidium parvum (xi) SEQUENCE DESCRIPTION: SEQ ID NO: 3:

```
CCCCCAAATT CTATTAATTG GGTGGAAGCT GGATGCGTGA ACCCAATAAG AAATCAAAAG    60

AATTGTGGGT CATGTTGGGC TTTCTCTGCT GTTGCAGCTT TGGAGGGAGC AACGTGTGCT   120

CAAACAAACC GAGGATTACC AAGCTTGAGT GAACAGCAAT TGTTGATTG CAGTAAACAA   180

AATGGCAACT TTGGATGTGA TGGAGGAACA ATGGGATTGG CTTTTCAGTA TGCAATTAAG   240

AACAAATATT TATGTACTAA TGATGATTAC CCTTACTTTG CTGAGGAAAA AACATGTATG   300

GATTCATTTT GCGAGAATTA TATAGAGATT CCTGTAAAAG CCTACAAATA TGTATTTCCG   360

AGAAATATTA ATGCATTAAA GACTGCTTTG GCTAAGTATG GACCAATTTC AGTTGCAATT   420

CAGGCCGATC AAACCCCTTT CCAGTTTTAT AAAAGTGGAG TATTCGATGC TCCTTGTGGA   480

ACCAAGGTTA ATCATGGAGT TGTTCTAGTT GAATATGATA TGGATGAAGA TACTAATAAA   540

GAATATTGGC TAGTAAGAAA TAGCTGGGGT GAAGCGTGGG GAGAGAAAGG ATACATCAAA   600

CTAGCTCTTC ATTCTGGAAA GAAGGGAACA TGTGGTATAT TGGTTGAGCC AGTGTATCCA   660

GTGATTAATC AATCAATA                                                 678
```

(2) INFORMATION FOR SEQ ID NO: 4:

(i) SEQUENCE CHARACTERISTICS:
        (A) LENGTH: 401 amino acids

-continued

```
        (B) TYPE: amino acids
        (C) STRANDEDNESS: single
        (D) TOPOLOGY: linear (ii) MOLECULE TYPE: protein (vi) ORIGINAL SOURCE:
        (A) ORGANISM: Cryptosporidium parvum (xi) SEQUENCE DESCRIPTION: SEQ ID NO: 4:

Met Asp Ile Gly Asn Asn Val Glu Glu His Gln Glu Tyr Ile Ser
 1               5                  10                  15

Gly Pro Tyr Ile Ala Leu Ile Asn Gly Thr Asn Gln Gln Arg Glu
                20                  25                  30

Pro Asn Lys Lys Leu Lys Asn Ile Ile Ala Thr Leu Ile Ala
                35                  40                  45

Ile Phe Ile Val Leu Val Val Thr Val Ser Leu Tyr Ile Thr Asn
                50                  55                  60

Asn Thr Ser Asp Lys Ile Asp Asp Phe Val Pro Gly Asp Tyr Val
                65                  70                  75

Asp Pro Ala Thr Arg Glu Tyr Arg Lys Ser Phe Glu Glu Phe Lys
                80                  85                  90

Lys Lys Tyr His Lys Val Tyr Ser Ser Met Glu Glu Glu Asn Gln
                95                 100                 105

Arg Phe Glu Ile Tyr Lys Gln Asn Met Asn Phe Ile Lys Thr Thr
               110                 115                 120

Asn Ser Gln Gly Phe Ser Tyr Val Leu Glu Met Asn Glu Phe Gly
               125                 130                 135

Asp Leu Ser Lys Glu Glu Phe Met Ala Arg Phe Thr Gly Tyr Ile
               140                 145                 150

Lys Asp Ser Lys Asp Asp Glu Arg Val Phe Lys Ser Ser Arg Val
               155                 160                 165

Ser Ala Ser Glu Ser Glu Glu Phe Val Pro Pro Asn Ser Ile
               170                 175                 180

Asn Trp Val Glu Ala Gly Cys Val Asn Pro Ile Arg Asn Gln Lys
               185                 190                 195

Asn Cys Gly Ser Cys Trp Ala Phe Ser Ala Val Ala Ala Leu Glu
               200                 205                 210

Gly Ala Thr Cys Ala Gln Thr Asn Arg Gly Leu Pro Ser Leu Ser
               215                 220                 225

Glu Gln Gln Phe Val Asp Cys Ser Lys Gln Asn Gly Asn Phe Gly
               230                 235                 240

Cys Asp Gly Gly Thr Met Gly Leu Ala Phe Gln Tyr Ala Ile Lys
               245                 250                 255

Asn Lys Tyr Leu Cys Thr Asn Asp Asp Tyr Pro Tyr Phe Ala Glu
               260                 265                 270

Glu Lys Thr Cys Met Asp Ser Phe Cys Glu Asn Tyr Ile Glu Ile
               275                 280                 285

Pro Val Lys Ala Tyr Lys Tyr Val Phe Pro Arg Asn Ile Asn Ala
               290                 295                 300

Leu Lys Thr Ala Leu Ala Lys Tyr Gly Pro Ile Ser Val Ala Ile
               305                 310                 315

Gln Ala Asp Gln Thr Pro Phe Gln Phe Tyr Lys Ser Gly Val Phe
               320                 325                 330

Asp Ala Pro Cys Gly Thr Lys Val Asn His Gly Val Val Leu Val
               335                 340                 345
```

```
Glu Tyr Asp Met Asp Glu Asp Thr Asn Lys Glu Tyr Trp Leu Val
                350                 355                 360

Arg Asn Ser trp Gly Glu Ala Trp Gly Glu Lys Gly Tyr Ile Lys
                365                 370                 375

Leu Ala Leu His Ser Gly Lys Lys Gly Thr Cys Gly Ile Leu Val
                380                 385                 390

Glu Pro Val Tyr Pro Val Ile Asn Gln Ser Ile
                395                 400
```

(2) INFORMATION FOR SEQ ID NO: 5:

(i) SEQUENCE CHARACTERISTICS:
        (A) LENGTH: 175 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Cryptosporidium parvum (xi) SEQUENCE DESCRIPTION: SEQ ID NO: 5:

```
Met Asp Ile Gly Asn Asn Val Glu Glu His Gln Glu Tyr Ile Ser
1               5                   10                  15

Gly Pro Tyr Ile Ala Leu Ile Asn Gly Thr Asn Gln Gln Arg Glu
                20                  25                  30

Pro Asn Lys Lys Leu Lys Asn Ile Ile Ala Thr Leu Ile Ala
                35                  40                  45

Ile Phe Ile Val Leu Val Val Thr Val Ser Leu Tyr Ile Thr Asn
                50                  55                  60

Asn Thr Ser Asp Lys Ile Asp Asp Phe Val Pro Gly Asp Tyr Val
                65                  70                  75

Asp Pro Ala Thr Arg Glu Tyr Arg Lys Ser Phe Glu Glu Phe Lys
                80                  85                  90

Lys Lys Tyr His Lys Val Tyr Ser Ser Met Glu Glu Glu Asn Gln
                95                  100                 105

Arg Phe Glu Ile Tyr Lys Gln Asn Met Asn Phe Ile Lys Thr Thr
                110                 115                 120

Asn Ser Gln Gly Phe Ser Tyr Val Leu Glu Met Asn Glu Phe Gly
                125                 130                 135

Asp Leu Ser Lys Glu Glu Phe Met Ala Arg Phe Thr Gly Tyr Ile
                140                 145                 150

Lys Asp Ser Lys Asp Asp Glu Arg Val Phe Lys Ser Ser Arg Val
                155                 160                 165

Ser Ala Ser Glu Ser Glu Glu Glu Phe Val
                170                 175
```

(2) INFORMATION FOR SEQ ID NO: 6:

(i) SEQUENCE CHARACTERISTICS:
        (A) LENGTH: 226 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Cryptosporidium parvum (xi) SEQUENCE DESCRIPTION: SEQ ID NO: 6:

```
Pro Pro Asn Ser Ile Asn Trp Val Glu Ala Gly Cys Val Asn Pro
 1               5                  10                  15

Ile Arg Asn Gln Lys Asn Cys Gly Ser Cys Trp Ala Phe Ser Ala
                20                  25                  30

Val Ala Ala Leu Glu Gly Ala Thr Cys Ala Gln Thr Asn Arg Gly
                35                  40                  45

Leu Pro Ser Leu Ser Glu Gln gln Phe Val Asp Cys Ser Lys Gln
                50                  55                  60

Asn Gly Asn Phe Gly Cys Asp Gly Gly Thr Met Gly Leu Ala Phe
                65                  70                  75

Gln Tyr Ala Ile Lys Asn Lys Tyr Leu Cys Thr Asn Asp Asp Tyr
                80                  85                  90

Pro Tyr Phe Ala Glu Glu Lys Thr Cys Met Asp Ser Phe Cys Glu
                95                  100                 105

Asn Tyr Ile Glu Ile Pro Val Lys Ala Tyr Lys Tyr Val Phe Pro
                110                 115                 120

Arg Asn Ile Asn Ala Leu Lys Thr Ala Leu Ala Lys Tyr Gly Pro
                125                 130                 135

Ile Ser Val Ala Ile Gln Ala Asp Gln Thr Pro Phe Gln Phe Tyr
                140                 145                 150

Lys Ser Gly Val Phe Asp Ala Pro Cys Gly Thr Lys Val Asn His
                155                 160                 165

Gly Val Val Leu Val Glu Tyr Asp Met Asp Glu Asp Thr Asn Lys
                170                 175                 180

Glu Tyr Trp Leu Val Arg Asn Ser Trp Gly Glu Ala Trp Gly Glu
                185                 190                 195

Lys Gly Tyr Ile Lys Leu Ala Leu His Ser Gly Lys Lys Gly Thr
                200                 205                 210

Cys Gly Ile Leu Val Glu Pro Val Tyr Pro Val Ile Asn Gln Ser
                215                 220                 225

Ile
226
```

(2) INFORMATION FOR SEQ ID NO: 7:

(i) SEQUENCE CHARACTERISTICS:
        (A) LENGTH: 345 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Carica (xi) SEQUENCE DESCRIPTION: SEQ ID NO: 7:

```
Met Ala Met Ile Pro Ser Ile Ser Lys Leu Leu Phe Val Ala Ile
 1               5                  10                  15

Cys Leu Phe Val Tyr Met Gly Leu Ser Phe Gly Asp Phe Ser Ile
                20                  25                  30

Val Gly Tyr Ser Gln Asn Asp Leu Thr Ser Thr Glu Arg Leu Ile
                35                  40                  45

Gln Leu Phe Glu Ser Trp Met Leu Lys His Asn Lys Ile Tyr Lys
                50                  55                  60

Asn Ile Asp Glu Lys Ile Tyr Arg Phe Glu Ile Phe Lys Asp Asn
```

```
                        65                   70                   75
Leu Lys Tyr Ile Asp Glu Thr Asn Lys Lys Asn Asn Ser Tyr Trp
                   80                   85                   90

Leu Gly Leu Asn Val Phe Ala Asp Met Ser Asn Asp Glu Phe Lys
                   95                  100                  105

Glu Lys Tyr Thr Gly Ser Ile Ala Gly Asn Tyr Thr Thr Thr Glu
                  110                  115                  120

Leu Ser Tyr Glu Glu Val Leu Asn Asp Gly Asp Val Asn Ile Pro
                  125                  130                  135

Glu Tyr Val Asp Trp Arg Gln Lys Gly Ala Val Thr Pro Val Lys
                  140                  145                  150

Asn Gln Gly Ser Cys Gly Ser Cys Trp Ala Phe Ser Ala Val Val
                  155                  160                  165

Thr Ile Glu Gly Ile Ile Lys Ile Arg Thr Gly Asn Leu Asn Glu
                  170                  175                  180

Tyr Ser Glu Gln Glu Leu Leu Asp Cys Asp Arg Arg Ser Tyr Gly
                  185                  190                  195

Cys Asn Gly Gly Tyr Pro Trp Ser Ala Leu Gln Leu Val Ala Gln
                  200                  205                  210

Tyr Gly Ile His Tyr Arg Asn Thr Tyr Pro Tyr Glu Gly Val Gln
                  215                  220                  225

Arg Tyr Cys Arg Ser Arg Glu Lys Gly Pro Tyr Ala Ala Lys Thr
                  230                  235                  240

Asp Gly Val Arg Gln Val Gln Pro Tyr Asn Glu Gly Ala Leu Leu
                  245                  250                  255

Tyr Ser Ile Ala Asn Gln Pro Val Ser Val Leu Glu Ala Ala
                  260                  265                  270

Gly Lys Asp Phe Gln Leu Tyr Arg Gly Ile Phe Val Gly Pro
                  275                  280                  285

Cys Gly Asn Lys Val Asp His Ala Val Ala Ala Val Gly Tyr Gly
                  290                  295                  300

Pro Asn Tyr Ile Leu Ile Lys Asn Ser Trp Gly Thr Gly Trp Gly
                  305                  310                  315

Glu Asn Gly Tyr Ile Arg Ile Lys Arg Gly Thr Gly Asn Ser Tyr
                  320                  325                  330

Gly Val Cys Gly Leu Tyr Thr Ser Ser Phe Tyr Pro Val Lys Asn
                  335                  340                  345

(2) INFORMATION FOR SEQ ID NO: 8:

(i) SEQUENCE CHARACTERISTICS:
        (A) LENGTH: 244 amino acids
        (B) TYPE: amino acid
        (C) STRANDEDNESS: single
        (D) TOPOLOGY: linear (ii) MOLECULE TYPE: protein (vi) ORIGINAL SOURCE:
         (A) ORGANISM: Plasmodium vinckei (xi) SEQUENCE DESCRIPTION: SEQ ID NO: 8:

Phe Pro Asp Ser Arg Asp Tyr Arg Ser Lys Phe Asn Phe Leu Pro
                    5                   10                   15

Pro Lys Asp Gln Gly Asn Cys Gly Ser Cys trp Ala Phe Ala Ala
                   20                   25                   30

Ile Gly Asn Phe Glu Tyr Leu Tyr Val His Thr Arg His Glu Met
```

|  |  |  | 35 |  |  |  | 40 |  |  |  | 45 |
|---|---|---|---|---|---|---|---|---|---|---|---|

Pro Ile Ser Phe Ser Glu Gln Gln Met Val Asp Cys Ser Thr Glu
            50                   55                 60

Asn Tyr Gly Cys Asp Gly Gly Asn Pro Phe Tyr Ala Phe Leu Tyr
            65                   70                 75

Met Ile Asn Asn Gly Val Cys Leu Gly Asp Glu Tyr Pro Tyr Lys
            80                   85                 90

Gly His Glu Asp Phe Phe Cys Leu Asn Tyr Arg Cys Ser Leu Leu
            95                  100              105

Gly Arg Val His Phe Ile Gly Asp Val Lys Pro Asn Glu Leu Ile
           110                 115              120

Met Ala Leu Asn Tyr Val Gly Pro Val Thr Ile Ala Val Gly Ala
           125                 130              135

Ser Glu Asp Phe Val Leu Tyr Ser Gly Gly Val Phe Asp Gly Glu
           140                 145              150

Cys Asn Pro Glu Leu Asn His Ser Val Leu Leu Val Gly Tyr Gly
           155                 160              165

Gln Val Lys Lys Ser Leu Ala Phe Glu Asp Ser His Ser Asn Val
           170                 175              180

Asp Ser Asn Leu Ile Lys Lys Tyr Lys Glu Asn Ile Lys Gly Asp
           185                 190              195

Asp Asp Asp Asp Ile Ile Tyr Tyr Trp Ile Val Arg Asn Ser Trp
           200                 205              210

Gly Pro Asn Trp Gly Glu Gly Gly Tyr Ile Arg Ile Lys Arg Asn
           215                 220              225

Lys Ala Gly Asp Asp Gly Phe Cys Gly Val Gly Ser Asp Val Phe
           230                 235              240

Phe Pro Ile Tyr
           244

(2) INFORMATION FOR SEQ ID NO: 9:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: synthetic oligonucleotide (ix) FEATURE:
        (A) NAME/KEY:   Y is C/T
            W is A/T
            S is C/G
        (B) LOCATION:
        (C) IDENTIFICATION METHOD:
        (D) OTHER INFORMATION:

(xi) SEQUENCE DESCRIPTION: SEQ ID NO: 9:

AAAGGATCCT GYGGNWSNTG YTGGGCNTT                                29

(2) INFORMATION FOR SEQ ID NO: 10:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: synthetic oligonucleotide (ix) FEATURE:

```
        (A) NAME/KEY:  S is C/G
                       K is G/T
                       W is A/T
                       R is A/G
        (B) LOCATION:
        (C) IDENTIFICATION METHOD:
        (D) OTHER INFORMATION:

(xi) SEQUENCE DESCRIPTION: SEQ ID NO: 10:

TTTGAATTCC CANSWRTTNY KNAYNATCCA RTA                              33

(2) INFORMATION FOR SEQ ID NO: 11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: synthetic oligonucleotide (xi) SEQUENCE DESCRIPTION: SEQ ID NO: 11:

CCAGGTACCA TGGACATAGG AAAC                                        24

(2) INFORMATION FOR SEQ ID NO: 12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: synthetic oligonucleotide (iv) ANTI-SENSE: YES (xi) SEQUENCE DESCRIPTION: SEQ ID NO: 12:

CCCTCTAGAT GCTTATATTG ATTG                                        24

(2) INFORMATION FOR SEQ ID NO: 13:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 13:

Cys Gly Ser Cys Trp Ala Phe
              5           7

(2) INFORMATION FOR SEQ ID NO: 14:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptides (ix) FEATURE:
        (A) NAME/KEY:  Xaa at 4 is Val/Ile
                       Xaa at 5 is Lys/Arg
        (B) LOCATION:
        (C) IDENTIFICATION METHOD:
        (D) OTHER INFORMATION:

(xi) SEQUENCE DESCRIPTION: SEQ ID NO: 14:
```

```
Tyr Trp Ile Xaa Xaa Asn Ser Trp
              5           8
```

(2) INFORMATION FOR SEQ ID NO: 15:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 15:

```
Val Arg Asn Ser Trp
              5
```

(2) INFORMATION FOR SEQ ID NO: 16:

(i) SEQUENCE CHARACTERISTICS:
        (A) LENGTH: 1203 base pairs
        (B) TYPE: nucleic acid
        (C) STRANDEDNESS: double
        (D) TOPOLOGY: linear (ii) MOLECULE TYPE: DNA (vi) ORIGINAL SOURCE:
        (A) ORGANISM: Cryptosporidium parvum (xi) SEQUENCE DESCRIPTION: SEQ ID NO: 16:

```
ATGGACATAG GAAACAACGT GGAAGAACAT CAGGAATATA TTTCTGGACC ATACATTGCA      60
TTAATTAATG GCACTAATCA ACAAAGGGAA CCGAATAAAA AGTTGAAAAA CATAATAATT     120
GCAACGTTGA TTGCAATCTT TATAGTTTTG GTTGTTACTG TATCTTTGTA TATTACTAAT     180
AACACCAGTG ACAAAATTGA CGATTTCGTA CCTGGTGATT ATGTTGATCC AGCAACTAGG     240
GAGTATAGAA AGAGTTTTGA GGAGTTCAAA AAGAAATACC ACAAAGTATA TAGCTCTATG     300
GAGGAGGAAA ATCAAAGATT TGAAATTTAT AAGCAAAATA TGAACTTTAT TAAAACAACA     360
AATAGCCAAG GATTCAGTTA TGTGTTAGAA ATGAATGAAT TTGGTGATTT GTCGAAAGAA     420
GAGTTTATGG CAAGATTCAC AGGATATATA AAAGATTCCA AAGATGATGA AAGGGTATTT     480
AAGTCAAGTA GAGTCTCAGC AAGCGAATCA GAAGAGGAAT TTGTTCCCCC AAATTCTATT     540
AATTGGGTGG AAGCTGGATG CGTGAACCCA ATAAGAAATC AAAAGAATTG TGGGTCATGT     600
TGGGCTTTCT CTGCTGTTGC AGCTTTGGAG GGAGCAACGT GTGCTCAAAC AAACCGAGGA     660
TTACCAAGCT TGAGTGAACA GCAATTTGTT GATTGCAGTA AACAAAATGG CAACTTTGGA     720
TGTGATGGAG GAACAATGGG ATTGGCTTTT CAGTATGCAA TTAAGAACAA ATATTTATGT     780
ACTAATGATG ATTACCCTTA CTTTGCTGAG GAAAAAACAT GTATGGATTC ATTTTGCGAG     840
AATTATATAG AGATTCCTGT AAAAGCCTAC AAATATGTAT TTCCGAGAAA TATTAATGCA     900
TTAAAGACTG CTTTGGCTAA GTATGGACCA ATTTCAGTTG CAATTCAGGC CGATCAAACC     960
CCTTTCCAGT TTTATAAAAG TGGAGTATTC GATGCTCCTT GTGGAACCAA GGTTAATCAT    1020
GGAGTTGTTC TAGTTGAATA TGATATGGAT GAAGATACTA ATAAAGAATA TTGGCTAGTA    1080
AGAAATAGCT GGGGTGAAGC GTGGGGAGAG AAAGGATACA TCAAACTAGC TCTTCATTCT    1140
GGAAAGAAGG GAACATGTGG TATATTGGTT GAGCCAGTGT ATCCAGTGAT TAATCAATCA    1200
ATA                                                                  1203
```